(12) United States Patent
Carroll et al.

(10) Patent No.: US 6,677,258 B2
(45) Date of Patent: *Jan. 13, 2004

(54) BREATHABLE COMPOSITE SHEET STRUCTURE AND ABSORBENT ARTICLES UTILIZING SAME

(75) Inventors: Nora Liu Carroll, Midlothian, VA (US); Hyun Sung Lim, Midlothian, VA (US); George Joseph Ostapchenko, Wilmington, DE (US); Shailaja R. Vaidya, Hockessin, DE (US); J. Michael Mc Kenna, Hockessin, DE (US); John Joseph Curro, Cincinnati, OH (US); Gary Dean Lavon, Middletown, OH (US); Richard L. Sparks, Cheasapeake, VA (US)

(73) Assignees: E. I. du Pont de Nemours and Company, Wilmington, DE (US); Proctor and Gamble, West Chester, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 110 days.

(21) Appl. No.: 09/194,378

(22) Filed: Nov. 25, 1998

(65) Prior Publication Data

US 2002/0019187 A1 Feb. 14, 2002

(51) Int. Cl.[7] .................. B32B 27/12; B32B 27/36; B32B 25/10
(52) U.S. Cl. .............. 442/394; 442/395; 442/398; 442/399
(58) Field of Search ............... 442/394, 395, 442/398, 399

(56) References Cited

U.S. PATENT DOCUMENTS 2,075,189 A    3/1937  Galligan et al. ............... 154/33

(List continued on next page.)

FOREIGN PATENT DOCUMENTS

AU    B-21721/95    1/1996   .......... B32B/27/08

(List continued on next page.)

OTHER PUBLICATIONS

U.S. patent application Ser. No. 08/359,986, McCormack et al., filed Dec. 20, 1994.

Thomas R. Ryle, Extrusion Coating and Lamination of Nonwovens, *Principles of Nonwovens*, TS1828.P66, 717–727, 1992.

*Primary Examiner*—Cheryl A. Juska
*Assistant Examiner*—Christopher C. Pratt

(57) ABSTRACT

A breathable composite sheet material, a method for making such a sheet material, and an absorbent article utilizing the sheet material are provided. The composite sheet material is comprised of a thermoplastic film adhered directly to a fibrous substrate. The thermoplastic film comprises at least 50% by weight of a polymer material from the group of block copolyether esters, block copolyether amides and polyurethanes. The substrate comprises a fibrous web of at least 50% by weight of polyolefin polymersynthetic fibers. The composite sheet exhibits a peel strength of at least 0.1 N/cm, a dynamic fluid transmission of less than about 0.75 $g/m^2$ when subjected to an impact energy of about 2400 $joules/m^2$, and a moisture vapor transmission rate, according to the dessiccant method, of at least 1500 $g/m^2/2$ hr. The absorbent article comprises: (a) a topsheet; (b) a backsheet; and (c) an absorbent core located between the topsheet and the backsheet; wherein the backsheet comprises the nonporous, substantially fluid impermeable moisture vapor permeable composite sheet material described above. The composite sheet material is oriented such that the film layer of the composite sheet material faces toward the absorbent core. The absorbent article may comprise a disposable diaper.

10 Claims, 4 Drawing Sheets

U.S. PATENT DOCUMENTS

| | | | |
|---|---|---|---|
| 3,025,199 A | 3/1962 | Harwood | 154/46 |
| 3,651,014 A | 3/1972 | Witsiepe | 260/75 |
| 3,763,109 A | 10/1973 | Witsiepe | 260/75 |
| 3,766,146 A | 10/1973 | Witsiepe | 260/75 |
| 3,848,594 A | 11/1974 | Buell | 128/284 |
| 3,860,003 A | 1/1975 | Buell | 128/287 |
| 3,904,706 A | 9/1975 | Hoeschele | 260/858 |
| 3,911,173 A | 10/1975 | Sprague, Jr. | 427/207 |
| 3,914,488 A | 10/1975 | Gorrafa | 428/397 |
| 3,929,135 A | 12/1975 | Thompson | 128/287 |
| 3,968,183 A | 7/1976 | Hayashi et al. | 260/860 |
| 4,107,364 A | 8/1978 | Sisson | 428/196 |
| 4,209,563 A | 6/1980 | Sisson | 428/288 |
| 4,324,246 A | 4/1982 | Mullane et al. | 128/287 |
| 4,342,314 A | 8/1982 | Radel et al. | 128/287 |
| 4,368,295 A | 1/1983 | Newton et al. | 525/166 |
| 4,381,781 A | 5/1983 | Sciaraffa et al. | 604/372 |
| 4,463,045 A | 7/1984 | Ahr et al. | 428/131 |
| 4,493,870 A | 1/1985 | Vrouenraets et al. | 428/245 |
| 4,515,595 A | 5/1985 | Kievit et al. | 604/385 A |
| 4,573,986 A | 3/1986 | Minetola et al. | 604/366 |
| 4,578,429 A | 3/1986 | Gergen et al. | 525/291 |
| 4,585,449 A * | 4/1986 | Karami | 604/378 |
| 4,610,678 A | 9/1986 | Weisman et al. | 604/368 |
| 4,634,625 A | 1/1987 | Franklin | 428/258 |
| 4,662,875 A | 5/1987 | Hirotsu et al. | 604/389 |
| 4,663,220 A | 5/1987 | Wisneski et al. | 428/221 |
| 4,673,402 A | 6/1987 | Weisman et al. | 604/368 |
| 4,695,278 A | 9/1987 | Lawson | 604/385 A |
| 4,704,115 A | 11/1987 | Buell | 604/385 A |
| 4,707,407 A | 11/1987 | Clark et al. | 428/361 |
| 4,725,481 A | 2/1988 | Ostapchenko | 428/213 |
| 4,739,012 A | 4/1988 | Hagman | 525/92 |
| 4,769,273 A | 9/1988 | Hoeschele et al. | 428/215 |
| 4,785,996 A | 11/1988 | Ziecker et al. | 239/298 |
| 4,789,699 A | 12/1988 | Kieffer et al. | 524/271 |
| 4,795,454 A | 1/1989 | Dragoo | 604/385.2 |
| 3,860,003 A | 4/1989 | Buell | 604/385.2 |
| 4,834,735 A | 5/1989 | Alemany et al. | 604/368 |
| 4,834,741 A | 5/1989 | Sabee | 604/385.2 |
| 4,842,666 A | 6/1989 | Werenicz | 156/161 |
| 4,846,815 A | 7/1989 | Scripps | 604/391 |
| 4,857,067 A | 8/1989 | Wood et al. | 604/389 |
| 4,868,062 A | 9/1989 | Hoeschele et al. | 428/423.1 |
| 4,869,724 A | 9/1989 | Scripps | 604/389 |
| 4,888,231 A | 12/1989 | Angstadt | 428/213 |
| 4,894,060 A | 1/1990 | Nestegard | 604/391 |
| 4,908,260 A | 3/1990 | Dodia et al. | 428/215 |
| 4,909,803 A | 3/1990 | Aziz et al. | 604/385.2 |
| 3,860,003 A | 6/1990 | Buell | 604/385.2 |
| 4,938,752 A | 7/1990 | Vrouenraets et al. | 604/370 |
| 4,938,753 A | 7/1990 | Van Gompel et al. | 604/385.2 |
| 4,938,757 A * | 7/1990 | Van Gompel et al. | 604/396 |
| 4,946,527 A | 8/1990 | Battrell | 156/60 |
| 4,988,344 A | 1/1991 | Reising et al. | 604/368 |
| 4,988,345 A | 1/1991 | Reising | 604/368 |
| 5,006,394 A | 4/1991 | Baird | 428/138 |
| 5,064,703 A | 11/1991 | Frankosky et al. | 428/95 |
| 5,137,537 A | 8/1992 | Herron et al. | 8/120 |
| 5,147,345 A | 9/1992 | Young et al. | 604/378 |
| 5,151,092 A | 9/1992 | Buell et al. | 604/385.2 |
| 5,234,423 A | 8/1993 | Alemany et al. | 604/385.2 |
| 5,326,612 A | 7/1994 | Goulait | 428/100 |
| 5,330,458 A | 7/1994 | Buell et al. | 604/385.1 |
| 5,358,500 A | 10/1994 | Lavon et al. | 604/385.2 |
| 5,393,599 A * | 2/1995 | Quantrille et al. | 428/284 |
| 5,422,172 A | 6/1995 | Wu | 428/230 |
| 5,445,862 A | 8/1995 | Kaneko et al. | 428/148 |
| 5,445,874 A | 8/1995 | Shehata | 428/252 |
| 5,447,783 A | 9/1995 | Horn | 428/216 |
| 5,514,470 A | 5/1996 | Haffner et al. | 428/246 |
| 5,518,801 A | 5/1996 | Chappell et al. | 428/152 |
| 5,520,980 A | 5/1996 | Morgan et al. | 428/246 |
| 5,532,053 A | 7/1996 | Mueller | 428/287 |
| 5,532,054 A | 7/1996 | Koba et al. | 428/294 |
| 5,650,223 A * | 7/1997 | Weinberger et al. | 442/62 |
| 5,662,978 A * | 9/1997 | Brown et al. | 428/57 |
| 5,861,074 A | 1/1999 | Wu | 156/229 |
| 5,865,823 A | 2/1999 | Curro | 604/367 |

FOREIGN PATENT DOCUMENTS

| | | | |
|---|---|---|---|
| EP | 295 694 | 12/1988 | |
| EP | 0 560 630 | 9/1993 | B32B/27/34 |
| EP | 700 779 | 7/1995 | |
| EP | 0 688 826 | 12/1995 | C08L/77/12 |
| EP | 708 212 | 4/1996 | |
| GB | 2 024 100 | 1/1980 | 5/2 |
| JP | 08-041316 | 2/1996 | C08L/75/04 |
| JP | 08-084749 | 4/1996 | A61F/13/54 |
| JP | 08-108504 | 4/1996 | A61F/13/15 |
| JP | 08-117270 | 5/1996 | A61F/13/15 |
| JP | 08-117271 | 5/1996 | A61F/13/15 |
| JP | 08-117280 | 5/1996 | A61F/13/15 |
| JP | 08-117281 | 5/1996 | A61F/13/15 |
| WO | WO 90/10424 | 9/1990 | A61F/13/00 |
| WO | WO 95/16562 | 6/1995 | B32B/5/24 |
| WO | WO 95/16746 | 6/1995 | C08L/67/02 |
| WO | WO 96/39031 | 12/1996 | A01N/25/34 |
| WO | WO 96/39032 | 12/1996 | A01N/25/34 |
| WO | WO 97/04955 | 2/1997 | B32B/3/26 |
| WO | WO 98/54389 | 12/1998 | D04H/13/00 |

* cited by examiner

BREATHABLE COMPOSITE SHEET STRUCTURE AND ABSORBENT ARTICLES UTILIZING SAME

FIELD OF THE INVENTION

This invention relates to a moisture vapor permeable, substantially liquid impermeable composite sheet structure useful in apparel, surgical drapes, sterile wraps, packaging materials, protective covers, construction materials, and personal care absorbent articles such as diapers and sanitary napkins. More particularly, the invention is directed to a moisture vapor permeable film and fibrous substrate that combine to form a composite sheet that is durable, strong, and flexible, that acts as a barrier to liquids, bacteria and odors, yet is also highly permeable to moisture vapor. The invention is also directed to an absorbent article having a backsheet made of the aforementioned composite sheet of the invention.

BACKGROUND OF THE INVENTION

Sheet materials used in making medical drapes, medical gowns and absorbent articles, such as diapers and sanitary napkins, must be both comfortable and substantially liquid impermeable. Manufacturing and use requirements for such products often demand that the sheet material also be strong and durable.

Infants and other incontinent individuals wear absorbent articles to receive and contain urine and other body exudates. Absorbent articles function both to contain the discharged materials and to isolate these materials from the body of the wearer and from the wearer's garments and bed clothing. Disposable absorbent articles having many different basic designs are known to the art. It is also known that the exterior of absorbent articles can be covered with a flexible, fluid and vapor impervious sheet to prevent any absorbed fluid from passing through the article and soiling adjacent articles such as clothing, bedding and the like. These outer covers, generally referred to as backsheets, are often constructed from fluid and vapor impervious films such as polyethylene.

While plastic films do an admirable job of containing liquids, they are not pleasing to the touch and they do not readily pass moisture vapor, which makes garments made with plastic films uncomfortable and irritating to the skin. Plastic films have been made more acceptable for apparel and personal care applications by creating micropores in the films to make breathable microporous films. In microporous films, moisture is transported through the films by way of small gaps or holes in the film. One notable microporous film composite is made from polytetrafluoroethylene that is adhered to a textile material with an adhesive, as disclosed in British Patent Application No. 2,024,100. Microporous films adhesively bonded to textile substrates have been used in a variety of apparel products, including absorbent articles, as disclosed in PCT Patent Publication Nos. WO 95/16562 and WO 96/39031.

Laminates of a microporous film and a fibrous textile substrate have a number of disadvantages, including that their manufacture requires a separate adhesive bonding step after the film is made, and that such laminates permit some seepage of fluids when used as the backsheet in an absorbent article. For example, when such microporous film laminates are used as a backsheet of a disposable diaper, the backsheet may permit the transmission of some urine through the pores in the backsheet when an infant wearing the diaper sits down. Liquid seepage through microporous film laminates is especially likely to occur when the microporous laminate is exposed to a fluid with a low surface tension, as for example when urine in a diaper is exposed to surfactants within the diaper itself.

When fluids seep through the pores of a microporous film, bacteria, viruses, and other microbes can pass through the film along with the fluids. Likewise, the passage of fluids through laminates made with microporous films, whether the fluids are liquid or gaseous, also increases the odors that emanate from such laminates. Microbial adsorbents have been added to some microporous films in an attempt to capture microbes passing through such films, as disclosed in PCT Patent Publication No. WO 96/39031. However it is difficult to distribute microbial adsorbents throughout a microporous film in a manner that will adsorb all microbes seeping through the holes in the film. Likewise, microbial adsorbents are unlikely to prevent the passage of odors through the pores in a microporous film.

Moisture vapor permeable films comprised of polyether block copolymers, like the film disclosed in U.S. Pat. No. 4,493,870, have an advantage in medical apparel and personal care applications because such films are non-porous and therefore substantially impermeable to fluids, but they permit the passage of moisture vapor. U.S. Pat. No. 4,725,481 suggests that such films may be attached to a textile fabric by adhesive bonding or melt bonding. However, the cost of making such films and then bonding the films to fibrous textile substrates has been high relative to microporous film laminates. In addition, known moisture vapor permeable films like the films disclosed in U.S. Pat. Nos. 4,725,481 and 5,445,874 do not readily adhere to many common nonwoven substrate materials, such as polyolefin-based nonwoven materials, without the application of a separate adhesive.

PCT Patent Publication No. WO 95/16746 (assigned to E. I. duPont de Nemours & Company (hereinafter "DuPont")) discloses a composition of a polyether block copolymer combined with a less costly thermoplastic homopolymer so as to make an overall film that is less costly, more heat sealable and more adherable to itself and other substrate materials. However, PCT Patent Publication No. WO 95/16746 does not disclose strong and durable composite sheets of thin breathable films that have been extruded directly onto fibrous substrates, nor does it disclose a method for making such composite sheets.

There is a need for a sheet material that acts as a barrier to fluids, yet is also highly permeable to moisture vapor. There is also a need for a sheet material that readily transmits moisture vapor, but significantly deters the passage of bacteria and odors associated with such fluids. There is a further need for such a moisture vapor permeable, fluid impermeable composite sheet material that is also durable, strong, and flexible enough to be used in absorbent articles, and can be produced in an economical fashion, i.e., without the use of adhesives to join the layers of the composite sheet in a separate step. Finally, there is a need for an absorbent article that incorporates such a moisture vapor permeable composite sheet in the article's backsheet, leg cuffs, waistshields, or other features.

SUMMARY OF THE INVENTION

The invention provides a moisture vapor permeable, substantially liquid impermeable composite sheet material comprising a fibrous substrate and a moisture vapor permeable thermoplastic film layer. The fibrous substrate is comprised of at least 50% by weight polyolefin polymer fibers. The moisture vapor permeable thermoplastic film layer is melt bonded directly to one side of said fibrous substrate. The composite sheet exhibits a peel strength of at least 0.1 N/cm, a dynamic fluid transmission of less than about 0.75 g/m$^2$ when subjected to an impact energy of about 2400 joules/m$^2$, and a moisture vapor transmission rate, according to the desiccant method, of at least 200 g/m$^2$/24 hr, preferably at least 1500 g/m$^2$/24 hr.

Preferably the film layer of the composite sheet has an average thickness of less than 50 microns and is comprised of at least 50% by weight of polymer selected from the group of block copolyether esters, block copolyether amides, polyurethanes, and combinations thereof. It is further preferred that the film layer be melt bonded to the substrate in the absence of an adhesive between the film layer and the substrate. The more preferred composite sheet has a peel strength of at least 0.15 N/cm, a film thickness of less than 30 microns, and a moisture vapor transmission rate, according to the dessicant method, of at least 2500 g/m$^2$/24 hr, and a dynamic fluid transmission of less than about 0.5 g/m$^2$ when subjected to an impact energy of about 2400 joules/m$^2$. The sheet is also substantially free of micoropores such that substantially no liquid moisture passes through the sheet when tested according to the liquid moisture seepage test, and the sheet acts as a barrier to the passage of microbes when tested according to the ISO 11607 standard for sterile packaging materials. The composite sheet should have a machine direction tensile strength and a cross direction tensile strength of at least 1 N/cm, and a machine direction elongation and a cross direction elongation of at least 30%.

According to one alternative embodiment of the invention the film layer may be bonded between two fibrous substrates. According to another alternative embodiment of the invention, the film layer of the composite sheet may comprise a moisture permeable film having multiple layers, each film layer being comprised of a different moisture vapor permeable thermoplastic polymer composition. One of the multiple layer film layers may comprise a substantially hydrophilic film layer and one of the film layers comprises a substantially hydrophobic film layer. According to yet another embodiment of the invention. the composite sheet may further include an additional layer of diverse construction and composition from the film layer and the fibrous layer, as for example, a microporous film.

According to the preferred embodiment of the invention, the film layer of the composite sheet is comprised at least 50% by weight of a Fraction A consisting essentially of polymer from the group of block copolyether esters, block copolyether amides, polyurethanes and combinations thereof, at least 5% by weight of a Fraction B consisting essentially of a polymer from the group of homopolymers of an alpha-olefin, copolymers or terpolymers containing an alpha-olefin and one or more other monomers, and a block copolymer of a vinylarene and a conjugated diene, and at least 0.1% by weight of a Fraction C consisting essentially of a compatibilizer for Fractions A and B. The film layer preferably comprises, by weight, 50% to 95% film Fraction A, 5% to 40% film Fraction B, and 0.1% to 15% film Fraction C. The film Fraction C preferably consists essentially of homopolymers, copolymers and terpolymers with backbones that are compatible with Fraction B, the backbones being grafted with a monomer having a functional group that is compatible with Fraction A. Film Fraction C is preferably a polymer with a backbone identical to Fraction B, which backbone is grafted with monomer selected from the group of alpha- and beta-ethylenically unsaturated carbonic acids and anhydrides, and derivatives thereof.

The invention also provides a method for making the breathable composite sheet material described above. Thermoplastic polymer selected from the group of block copolyether esters, block copolyether amides, polyurethanes, and combinations thereof is initially mixed. Next, the mixture is simultaneously melted and mixed, and is then melt extruded through a flat film die. The molten mixture is coated directly onto a moving fibrous substrate and is then forced into intimate contact with the fibrous substrate. The molten polymer may be forced into intimate contact with the substrate by passing the polymer coated substrate between cooled nip rollers or by passing the substrate over a vacuum suction inlet. The composite sheet is finally collected on a collection roll.

Finally, the invention provides an absorbent article comprising (a) a topsheet; (b) a backsheet; and (c) an absorbent core located between the topsheet and the backsheet; wherein the backsheet comprises the non-porous, substantially fluid impermeable, moisture vapor permeable composite sheet material described above. Preferably, the composite sheet material is oriented such that the film layer of the composite sheet material faces toward said absorbent core. Where the film layer of the composite sheet comprises a multiple layer film with a substantially hydrophilic elastomer film layer and a substantially hydrophobic elastomer film, the substantially hydrophilic elastomer film is preferably located between the substantially hydrophobic elastomer film and the fibrous substrate. Alternatively, the film layer may further comprise a third film layer comprising a substantially hydrophobic elastomer film located between the substantially hydrophilic elastomer film and the fibrous substrate. The absorbent article may comprise a disposable diaper.

BRIEF DESCRIPTION OF THE DRAWINGS

The accompanying drawings, which are incorporated in and constitute a part of this specification, illustrate the presently preferred embodiments of the invention and, together with the description, serve to explain the principles of the invention.

DETAILED DESCRIPTION OF THE INVENTION

Reference will now be made in detail to the presently preferred embodiments of the invention, examples of which are illustrated below.

Figure 1:
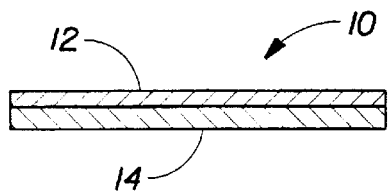
FIG. 1 is a cross-sectional view of the composite sheet structure of the invention.

The liquid impermeable, moisture vapor permeable composite sheet structure of the invention is shown in FIG. 1.

The composite sheet 10 is comprised of a fibrous substrate 14 to which a moisture vapor permeable and substantially liquid impermeable film 12 is directly adhered. Such composite sheets are sometimes referred to as laminate structures. The moisture permeable film is substantially free of pinholes or pores, yet still has a relatively high rate of moisture vapor transmission. As used herein, "pinholes" means small holes inadvertently formed in a film either during manufacture or processing of the film, while "pores" means small holes in a film that are intentionally formed in the film in order to make the film porous to air, moisture vapor or liquids. In the preferred embodiment of the invention, the moisture vapor permeable, substantially liquid impermeable film is a polyether block copolymer such as copolymers comprised of block copolyether esters, block copolyether amides, polyurethanes or combinations thereof. The fibrous substrate 14 is preferably comprised of synthetic polymer fibers in a form to which the moisture vapor permeable film can be directly adhered. The substrate 14 may be a woven or nonwoven structure, but for cost reasons, nonwoven textile structures are preferred for most applications. In an alternative embodiment of the invention shown in FIG. 2, the composite sheet structure may be comprised of a moisture permeable film layer 12 with two fibrous substrates 14 and 16, each comprised of synthetic polymer fibers, directly adhered on opposite sides of the film layer.

According to another embodiment of the invention, a thin layer of a block copolymer selected from a group comprising polyethers, polyamides and polyurethanes or a combination thereof could be used in conjunction with a microporous film to form a laminate film structure. Such a structure should overcome a number of the drawbacks associated with microporous films, namely bacteria and liquid seepage and high moisture impact values, without sacrificing the relatively high MVTR values, often >4,000 g/m$^2$/24 hr, obtainable with some microporous films. The moisture vapor permeable films of the composite sheet of the present invention can be made compatible with polyolefin nonwoven materials and can also be made compatible with current microporous film compositions, such as those of polyolefinic composition. The moisture vapor permeable film layer of the composite sheet of the present invention and a microporous film can be joined via adhesive lamination or potentially by direct extrusion coating. The moisture vapor permeable film could be combined with a fibrous substrate in a fashion consistent with the present invention. This fibrous substrate and moisture vapor permeable substantially liquid impermeable film and microporous film can be joined, in a fashion consistent with the present invention, with a nonwoven sheet bonded to the first side of the moisture vapor permeable, substantially liquid impermeable film layer and with a microporous film laminated to the opposing side of the film layer.

Alternatively, the process by which microporosity is incorporated into current polyolefin type microporous films, such as Exxon Exxaire (Catalog No. XBF-100W), could be utilized to impart microporosity to a layer of moisture permeable film in the composite sheet of the present invention, e.g., by the incorporation of a material such as calcium carbonate into the film layer. This would result in a moisture vapor permeable film layer comprised essentially of polymer from the group of block copolyether esters, block copolyether amides, polyurethanes or combinations thereof, with micropores incorporated therein. This film layer could then be formed into a laminate structure with thin layers of a moisture vapor permeable nonporous film on one or both sides of the microporous film. Additionally, a fibrous substrate could be bonded to such a film laminate structure in a fashion consistent with the present invention.

A particularly preferred nonwoven material for the fibrous substrates 14 and 16 is a fibrous polyolefin nonwoven web. Suitable polyolefin materials include polypropylene and polyethylene spunbonded webs, scrims, woven slit films, carded webs, flashspun webs, and woven or nonwoven sheets comprised of blends of polyolefin fibers or of polyolefin fibers and other fibers. Webs of polyolefin fibers can be made with a variety of desirable properties, including good vapor permeability, flexibility, softness and strength. Where the composite sheet 10 is to be used in an absorbent article, the substrates 14 and/or 16 should preferably have a tensile strength of at least 1 N/cm and an elongation of at least 30% in both the machine and cross directions. The machine direction is the long direction within the plane of the sheet, i.e., the direction in which the sheet is produced. The cross direction is the direction within the plane of the sheet that is perpendicular to the machine direction. More preferably, the fibrous substrates have a tensile strength of at least 1.5 N/cm and an elongation of at least 50% in both the machine and cross directions. Preferably, the fibrous substrate also has a porous structure that enhances both moisture permeability through the composite sheet and physical bonding between the film and substrate layers of the composite sheet.

One polyolefin sheet material that has been advantageously used for the fibrous substrate in the invention is TYPAR® spunbonded polypropylene sheet material. TYPAR® is a registered trademark of DuPont. Another fibrous sheet material that has been advantageously used in the composite sheet of the invention is a carded, thermally-bonded polypropylene nonwoven material commercially available from Fiberweb of Simpsonville, S.C., under the trade designation HEC. Substrates 14 and 16 may alternatively be comprised of webs of other synthetic polymer materials such as polyesters or polyamides, bicomponent fibers made of a polyolefin and one or more other polymers, or blends of polyolefin fibers and fibers comprised of other synthetic materials or other natural fibers such as cotton or cellulose fibers.

Film layer 12 of the composite sheet structure 10 is a moisture vapor permeable and substantially liquid impermeable film. The film layer is preferably extruded directly onto the fibrous substrate 14 and it is thereby adhered to the substrate 14 without the application of an additional adhesive. Film layer 12 comprises a thermoplastic polymer material that can be extruded as a thin, continuous, nonporous, substantially liquid impermeable moisture vapor permeable film. Layer 12 is preferably comprised primarily of a block polyether copolymer, such as a polyether ester copolymer, a polyether amide copolymer, a polyurethane copolymer, or a combination thereof. Preferred copolyether ester block copolymers for film layer 12 are segmented elastomers having soft polyether segments and hard polyester segments, as disclosed in U.S. Pat. No. 4,739,012 (assigned to DuPont). Suitable polyether ester block copolymers are sold by DuPont under the name Hytrel®. Hytrel® is a registered trademark of DuPont. Suitable copolyether amide copolymers for film layer 12 are copolyamides available under the name Pebax® from Atochem Inc. of Glen Rock, N.J., USA. Pebax® is a registered trademark of Elf Atochem, S.A. of Paris, France. Suitable polyurethanes for use in film layer 12 are thermoplastic urethanes available under the name Estane® from The B. F. Goodrich Company of Cleveland, Ohio, USA. A preferred composite sheet material is one wherein the film Fraction A is a block copolyether ester, film Fraction B is polypropylene, film Fraction C is a grafted polymer having a backbone of polypropylene that is grafted with maleic anhydride, and the substrate is a carded fibrous web comprised of at least 75% by weight polypropylene.

The mixing of the thermoplastic polymer or blends of polymers that comprise the film layer of the sheet structure of the invention can be conducted according to methods and techniques known in the art, e.g., by physical tumble blending followed by extrusion and mixing in a single screw extruder equipped with a mixing head such as those available from Davis-Standard Corp. (Pawcatuck, R.I., USA) or a twin screw compounding extruder such as those available from Warner-Pfliederer (Ramsey, N.J., USA) and Bersdorf Corporation (Charlotte, N.C., USA). Alternatively, loss in weight or volumetric feeders such as those available from K-Tron America (Pitman, N.J., USA) may be used to control the composition being fed to the extruders.

The composite sheet 10 is preferably prepared by an extrusion coating process. In the extrusion coating process, a uniform molten extrudate is first coated on the fibrous substrate material. The molten polymer and the substrate are brought into more intimate contact as the molten polymer cools and bonds with the substrate. Such contact and bonding may be enhanced by passing the layers through a nip formed between two rolls. Alternatively, the molten polymer may be pulled into contact with the fibrous substrate by passing the coated substrate over a suction inlet such that the vacuum pulls the molten polymer into contact with the substrate as the polymer cools and bonds with the substrate. The bonding may be further enhanced by subjecting the surface of the substrate that is to contact the film to surface treatment, such as corona treatment, as is known in the art and described in *Modern Plastics Encyclopedia Handbook*, p. 236 (1994), which is hereby incorporated by reference.

Figure 3:
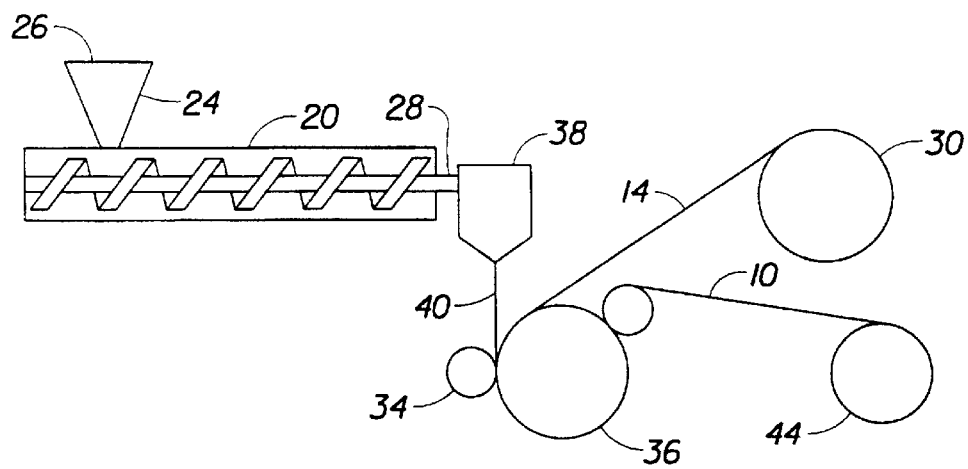
FIG. 3 is a schematic representation of a process by which the composite sheet structure of the invention is made.

One preferred means for applying the film layer 12 to the substrate 14 is illustrated in FIG. 3. As can be seen in FIG. 3, the thermoplastic polymer is fed in pellet form, along with any additives, into the inlet 26 of the extruder hopper 24. The polymer is melted and mixed in the screw extruder 20 at a screw speed in the range of 10 to 200 rpm, depending on the dimensions of the extruder and the properties of the polymer, and the melted mixture is discharged from the extruder under pressure through the heated line 28 to a flat film die 38. The polymer is discharged at a temperature above the melting temperature of the mixture, and preferably at a temperature in the range of 180° to 240° C. The polymer extrusion melt 40 discharging from the flat film die 38 coats the fibrous substrate 14.

Figure 2:
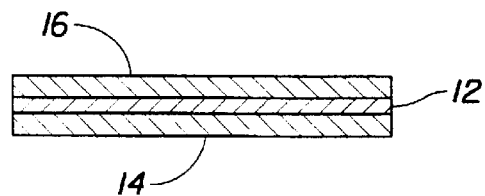
FIG. 2 is a cross-sectional view of a composite sheet structure according to an alternative embodiment of the invention.

Preferably, the substrate passes under the die at a speed that is coordinated with the speed of the extruder so as to obtain a desired film thickness. The coated substrate enters a nip formed between the rolls 34 and 36, which rolls are maintained at a temperature selected to obtain a composite sheet with a desired peel strength and moisture vapor permeability. The temperature of the rolls 34 and 36 is within the range of 10° to 120° C. As will be discussed below, higher roll temperatures have been found to yield a composite sheet with a higher peel strength, while lower roll temperatures have been found to yield composite sheets with a higher moisture vapor permeability. Preferably, roll 34 is a smooth rubber roller with a low-stick surface coating while the roll 36 is a metal roll. A textured embossing roll may be used in place of the metal roll for the roll 36 if a composite sheet with a more textured film layer (and higher surface area) is desired. Passing the coated substrate through the nip formed between cooled rolls 34 and 36 quenches the polymer melt while at the same time compressing the polymer melt 40 into and against the fibrous substrate 14. The nip pressure should be set high enough that the desired peel strength between the film and the substrate is achieved, but not so high that pinholes are formed in the film. The cooled polymer forms the film layer 12 of composite sheet 10, which composite sheet is collected on a collection roll 44. If a trilaminate product like that shown in FIG. 2 is desired, an additional substrate material 16 can be laid on the other side of the extruded polymer melt 40 as the polymer passes between rolls 34 and 36.

Alternatively, a vacuum process can be applied in order to compress the polymer melt 40 against the substrate material. The vacuum process is similar to conventional extrusion coating except that vacuum is used to bond the two substrates instead of nip rolls. The film is sucked into the fibrous substrate by applying a vacuum force against the underside of the substrate. The vacuum process optimizes adhesion while also producing products with good loft and hand.

According to another embodiment of the invention the film layer 12 may be a moisture vapor permeable, substantially liquid impermeable multiple layer film structure. Such a film may be coextruded with layers comprised of the one or more of the above described preferred thermoplastic film materials described herein. Such multiple layer moisture permeable films are disclosed in U.S. Pat. No. 4,725,481 (assigned to DuPont), which is hereby incorporated by reference. Multiple layer films are especially useful in the composite sheet of the invention where it is desirable for the film layer 12 to have different properties on its different sides. For example, a composite sheet could be made with a bicomponent film layer 12 having one side made of a moisture vapor permeable polymer material that thermally bonds well to the fibrous substrate 14 and an opposite side comprised of another moisture vapor permeable polymer that bonds well to materials to which the composite sheet is to be applied. It is anticipated that a moisture vapor permeable film of three or more co-extruded layers could be utilized for the film layer of the composite sheet of the invention in order to obtain an overall desired set of physical and aesthetic properties for the composite sheet.

The composite sheet 10 is especially useful as a component in disposable absorbent articles. As used herein, the term "absorbent article" refers to devices which absorb and contain body exudates, and, more specifically, refers to devices which are placed against or in proximity to the body of the wearer to absorb and contain the various exudates discharged from the body. Absorbent articles include disposable diapers, incontinence briefs, incontinence undergarments, incontinence pads, feminine hygiene garments, training pants, pull-on garments, and the like. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). Composite sheet 10 has physical properties that make the sheet especially useful as the outside "backsheet" of a disposable absorbent article, which properties include the composite sheet material's permeability to moisture vapor, its substantial impermeability to liquids, and its strength and durability. The ability of the composite sheet 10 to readily transmit moisture vapor means that hygiene products incorporating the composite sheet 10 as the product's backsheet material are comfortable to the wearer. The composite sheet's impermeability to fluids allows the sheet to completely contain bodily fluids even when the sheet is subjected to a dynamic impact of the type experienced when a baby or other person wearing a wet absorbent article sits down hard. The strength and durability of the composite sheet 10 permits the sheet to remain intact even after being stretched, rolled and pulled in the process of manufacturing an absorbent article.

It is believed that the moisture vapor transmission rate ("MVTR") of a composite sheet material used as the backsheet of an absorbent article is important in reducing humidity and temperature inside the absorbent article, thereby reducing the incidence of heat rash and other skin problems associated with such environmental conditions. For example, in order to reduce rash inducing humidity and heat buildup within a disposable absorbent article, it has been found that at least a portion of the article's backsheet, and preferably the entire backsheet should have a moisture vapor transmission rate of at least about 1500 $g/m^2/24$ hr. as measured by the desiccant MVTR measurement method described in the examples below. The composite sheet material of the present invention is capable of delivering an MVTR, as measured by the desiccant method, of at least about 1500 $g/m^2/24$ hr, and composite sheets according to the invention can deliver an MVTR greater than 4000 $g/m^2/24$ hr.

In the composite sheet of the present invention, moisture vapor transmission is enhanced because the moisture permeable film layer 12 is extruded directly onto the nonwoven substrate 14. This direct extrusion improves moisture transmission for a number of reasons. First, direct extrusion makes it possible to make composite sheets with very thin film layers, often with an average thickness of less than 30 microns. These thin films are highly permeable to moisture vapor but they are still substantially impermeable to liquids. Second, because the film layer of composite sheet 10 is extrusion coated directly onto the substrate 14 without the use of an adhesive, there is no adhesive layer to hinder moisture vapor transmission through the composite sheet. Finally, film layer 12 is extruded onto substrate 14 and passed through a nip such that the film presses into the pores and contours of the substrate. This process results in a film layer 12 that has a surface facing substrate 14 that is highly textured so as to have a high surface area.

A cross section of a sample of the composite sheet material of the present invention, made as described in Example 8, was photographed at a magnification level of 500× using a scanning electron microscope (SEM). An SEM photomicrograph of a section of the sample that was 484 microns long in the direction of the boundary between the film layer 12 and the substrate 14 was enlarged and carefully measured using calipers. The film interface had a total length of 871 microns, of which 411 microns of the interface was adhered directly to fibers of the substrate 14 and 460 microns of the interface was open to the pore spaces within the substrate. It is believed that the high surface area on the substrate side of the film layer 12 further enhances moisture vapor flux through the composite sheet 10.

The composite sheet of the present invention exhibits the important property that it is substantially impermeable to liquids under conditions that are normally associated with the use of absorbent articles and protective apparel. The liquid impermeability of the composite sheet 10 has been characterized according to a number of tests, including a liquid moisture seepage test, a dynamic barrier test, and a microbial barrier test.

The liquid moisture seepage test visually demonstrates the substantial liquid impermeability of the composite sheet 10. As described in the example below, this test determines whether a solution of food dye, isopropyl alcohol and water passes through a sheet material. As can be seen in Examples 8–17 below, the dye in alcohol solution did not pass through the composite sheet 10 of the present invention. On the other hand, when the same test was conducted on a sheet comprised of a microporous film laminated to a nonwoven substrate, dye solution seepage was apparent (Comparative Example 1).

The dynamic fluid impact test demonstrates the ability of the composite sheet 10 to resist liquid transmission when used as a backsheet in an absorbent article. The dynamic fluid impact test described in the examples below is designed to mimic the energy per unit area that an infant imparts to a diaper backsheet when abruptly going from a standing to a sitting position. Suitable sheet materials for a diaper backsheet should exhibit substantially zero dynamic fluid transmission (i.e., less than 1 $g/m^2$) when subjected to an impact energy of about 1000 joules/$m^2$, as is the case for the composite sheet 14 of the invention. More preferably, diaper backsheets exhibit substantially zero dynamic fluid transmission when subjected to an impact energy of 2400 joules/$m^2$ or more. As reported in Examples 8–17 below, these examples of the composite sheet of the invention passed less than 0.4 $g/m^2$ of water when subjected to an impact energy of about 2400 joules/$m^2$.

The ability of the composite sheet 10 to act as a barrier to liquids also prevents the passage of most odors, bacteria, or other microbes through the sheet. When a microporous film was tested according to a bacteria flux test used for evaluating porous sterile packaging materials (ASTM F 1608-95) (Comparative Example 1), the material did not pass this test because bacteria was found to pass through the sheet. On the other hand, the composite sheet 10 of the invention, by being impermeable to air during a one hour air porosity test (See Gurley Hill data in Examples 8, 9, 12, 13, 16 and 17), satisfies the microbial barrier requirement for impermeable sterile packaging materials, as set forth in ISO standard 11607, section 4.2.3.3.

The strength and durability of composite sheet 10 makes this sheet especially suitable for absorbent articles. This strength and durability allow the composite sheet 10 to remain intact even after being stretched, rolled, compressed and pulled during the process of manufacturing an absorbent article. It is also important that the composite sheet be strong and durable enough to remain intact when stretched, pulled and wetted during wearing of an article made using composite sheet 10 as the backsheet. The strength and durability of composite sheet 10 has been characterized in terms of (1) tensile strength, (2) the degree to which the sheet will stretch before breaking (known as "elongation"), and (3) the amount of force required to peel the moisture vapor permeable film from the fibrous substrate of the composite sheet (known as "peel strength" or "delamination strength").

Tensile strength is determined by measuring the tensile force required to rupture a sample of sheet material. Elongation is a measure of the amount that a sample of sheet material will stretch under tension before the sheet breaks. The elongation is the length just prior to break expressed as a percentage of the original sample length. Preferably, a composite sheet material that is to be used as the backsheet in an absorbent article has a tensile strength of at least 1 N/cm and an elongation of at least 30% in both the machine and cross directions. More preferably, if the composite sheet of the invention is to be used as the backsheet in an absorbent article, it should have a tensile strength of more than 1.5 N/cm and an elongation of at least 50% in both machine and cross directions. In the composite sheet of the present invention, the tensile properties and elongation properties of the composite sheet are largely dependent on the tensile and elongation properties of the fibrous substrate. A sheet material with the preferred tensile strength and elongation remains intact when wrapped around rollers at high speed during manufacture of absorbent articles. The elongation also makes the articles more comfortable to wearers because the articles have some give so as to be more conformable to a wearer's body shape because a sheet material with this elongation generally has some elasticity. As can be seen in Examples 8–17 below, the composite sheet 10 of the invention has a tensile strength of about 11 N/cm in the machine direction and 2 N/cm in the cross direction, and an elongation of from 59% to 87% in the machine direction and 67% to 108% in the cross direction. The preferred polyether block copolymer film of the invention provides a degree of elasticity to a composite sheet material that makes the sheet especially useful in an absorbent article.

Peel strength is a measure of the force required to delaminate the moisture permeable film from the fibrous substrate of a composite sheet. When the composite sheet 10 is used as a backsheet in a disposable absorbent article, such as a diaper, it is important that the composite sheet have a peel strength of at least 0.15 N/cm, and more preferably at least 0.20 N/cm, so that the sheet will not delaminate during manufacture of the article or during use. Such a peel strength is especially difficult to achieve when an adhesive is not used to attach the moisture vapor permeable film to the fibrous substrate. Good peel strength is even more difficult to achieve when the moisture vapor permeable film is chemically incompatible with the fibrous substrate, as is the case when a moisture permeable film comprised solely of a polyether ester block copolymer is coated on a polyolefin-based substrate. "Compatibility" of thermoplastic materials is an art-recognized term that refers, generally, to the degree to which the thermoplastic materials are miscible and/or interact with each other. Similarly, "incompatible" materials, as used herein, means polymer materials that are substantially immiscible or do not interact with each other. Incompatible materials do not wet each other well, nor do they adhere well to each other, even when heated.

Applicants have found that it is possible to greatly improve the peel strength between a moisture permeable film and a fibrous substrate by optimizing the physical bonding between the film and the substrate and/or by making the film and the substrate more chemically compatible. As is apparent in Examples 8–17 below, the composite sheet of the invention generally has a peel strength of from 0.3 N/cm to 0.6 N/cm, and a peel strength as high as a full bonding strength greater than 0.75 N/cm, which is the degree of bonding above which the film or the substrate will rupture before delamination occurs.

It has been found that physical bonding of the moisture vapor permeable film and the fibrous substrate can be greatly enhanced by selecting materials and bonding conditions that encourage the polymer film to physically bind with the fibers of the fibrous substrate. It has been especially surprising to find that good peel strength between the film and substrate can be attained by improving the physical bonding between the film and substrate layers, even where the layers are not chemically compatible and the molten polymer of the moisture vapor permeable film is a poor vetting agent for the fibrous substrate.

It has been found that the use of highly fibrous substrate materials, such as a carded web, improves physical bonding between the film and substrate layers of the composite sheet 10. It has also been found that the use of a polymer for the film layer that is sufficiently fluid in its molten state to intertwine with the fibers of the substrate, but not so fluid as to run out through the fiber substrate, also improves the peel strength of the composite sheet.

Extrusion coating and bonding conditions have also been found to have a great impact on the peel strength between the moisture vapor permeable film and the fibrous substrate of the composite sheet. Specific conditions that have been found to have a significant impact on the peel strength include the temperature of the melt 40 as it exits the die 38, the spacing between the die and the nip, the pressure of the nip, the temperature of the nip rolls 34 and 36, and the thickness of the film laid down on the substrate. It has been found that a polymer melt temperature in the range of 180° to 240° C. promotes excellent bonding of a polyether ester based moisture permeable film to a nonwoven polyolefin fibrous substrate. These relatively high polymer melt temperatures are thought to decrease the viscosity of the polymer film at the nip such that more of the film's polymer penetrates into the fibrous substrate as the composite sheet passes through the nip. Minimizing the spacing between the die and the nip has also been found to improve bonding in the composite sheet. It is postulated that the decreased die to nip spacing helps to maintain the elevated temperature of the polymer film layer as the film layer enters the nip so as to improve physical bonding between the film and substrate layers in the nip for the reasons just discussed above. As can be seen in Examples 18–35, a die to nip spacing of about 9 cm can be used to produce a composite sheet with good peel strength, depending upon the other processing conditions applied.

The bonding conditions at the nip itself should also be controlled so as to improve the physical bonding between the moisture permeable film and the fibrous substrate. As can be seen in Examples 25 and 31, when other bonding conditions are kept the same, an increase in the pressure applied at the nip improves the peel strength of the composite sheet. Maintaining the nip rolls at a temperature greater than ambient temperature in the range of 40° to 110° C. has also been found to improve physical bonding between the layers of the composite sheet material. As can be seen in Examples 28, 29 and 30, increasing the temperature of the rolls 34 and 36 (FIG. 3) improves the peel strength of the composite sheet when other bonding conditions are kept constant. Applicants believe that the elevated temperature of the nip rolls helps to keep the moisture vapor permeable film layer fluid enough that the substantial pressure applied at the nip will cause the polymer of the film to more effectively penetrate into the void spaces in the fibrous substrate and become more effectively entangled with the substrate.

Physical bonding of moisture permeable film layer 12 to fibrous substrate 14 has been found to improve with film thickness. Applicants believe that this improvement is a result of the thicker film's better ability to retain heat during the bonding process which serves to decrease the viscosity of the moisture permeable polymer film material as it enters the nip. As discussed above, it is believed that a less viscous and more fluid film more easily penetrates the substrate to intertwine with substrate fibers before solidifying. However, thicker films tend to have lower moisture vapor transmission rates and they are also more expensive to produce. Thus, the peel strength that can be gained by making the moisture permeable film layer 12 thicker must be balanced against possible loss in moisture vapor transmission and the added expense of a thicker film. It is believed that at a given film thickness, the use of a lower basis weight fibrous substrate material should also help to increase peel strength.

The chemical interaction between the moisture permeable film layer 12 and the fibrous substrate 14 appears to impact both physical and chemical bonding between the layers of the composite sheet. If the polymers of the film layer 12 and the substrate 14 are chemically compatible, the polymer of the film layer will wet the polymer of the fibers to a greater extent, which, in turn, improves physical bonding between the layers of the composite sheet. Making the polymers of the moisture permeable film layer and the fibrous substrate more compatible also increases the level of chemical attraction between the layers of the composite sheet.

Chemical interaction of the moisture vapor permeable film and the fibrous substrate is enhanced by selecting film materials and substrate materials that are compatible with each other. The preferred polyether block copolymer moisture permeable films are compatible with ester-based fibrous substrates, such as polyester webs, and thus adhere well to polyesters. However, such polyether-based block copolymer films are not chemically compatible with the stronger and less costly polyolefin webs that are more suitable for use in disposable absorbent articles. It has unexpectedly been found that the addition of a relatively small amount of certain select thermoplastic polymer materials to the polyether block copolymer can dramatically improve bonding between a polyether block copolymer film and an otherwise incompatible substrate, such as a polyolefin-based web, without unduly impacting the liquid impermeability, the moisture vapor transmission ability, or the strength and durability of the film. It has been found that a thermoplastic polymer can be mixed with a polyether block copolymer to make it possible to better extrude the polyether copolymer directly onto fibrous substrates not ordinarily compatible with a copolyether block copolymer and obtain excellent bonding between the film and substrate layers without the application of an additional adhesive or bonding agent.

A suitable apparatus for combining the block polyether copolymer (referred to below as "Fraction A") and a thermoplastic (referred to below as "Fraction B") that is compatible with the substrate 14, is illustrated in FIG. 3. Fraction A and Fraction B are mixed by physically blending pellets of Fraction A and Fraction B and then pouring the mixture into the inlet 26 of extruder hopper 24. The pellets are fed into a heated screw extruder 20 where they are melted and further mixed. Fractions A and B are ordinarily not compatible with each other such that Fraction B will not by itself distribute well through Fraction A as is required for good uniform moisture vapor transmission properties of film layer 12 and good uniform adhesion between layer 12 and the fibrous substrate layer 14. However, it has been found that the addition of a small amount of certain compatibilizers can greatly improve the mixing of Fractions A and B.

Preferably, the compatibilizer is a thermoplastic material that serves to improve the processing and uniformity of the mixture of Fractions A and B. The compatibilizer has a character that makes it simultaneously soluble or reactive with Fraction B and interactive with Fraction A, thereby producing a dispersion of globules of Fraction B which are adhered to the Fraction A matrix. The compatibilizer (hereinafter "Fraction C") is chosen according to the nature of Fraction B. Fraction C should have a backbone that is compatible with, and is preferably identical to, Fraction B and a functional group that is compatible with or interacts with Fraction A. The addition of Fraction C changes the morphology of the composition of the mixture such that Fraction B distributes uniformly in Fraction A in the form of globules that are chemically and/or physically bonded to the Fraction A matrix.

Fraction A consists of at least 50% by weight of a block copolyether ester, a block copolyether amide, a polyurethane, or a combination thereof. Preferred copolyether ester block copolymers for Fraction A are segmented elastomers having soft polyether segments and hard polyester segments, as disclosed in U.S. Pat. No. 4,739,012 (assigned to DuPont), such as the polyether ester block copolymers sold by DuPont under the name Hytrel®. Suitable copolyether amide copolymers for use in the Fraction A include copolyamides available under the name Pebax® from Atochem Inc. of Glen Rock, N.J. Suitable polyurethanes for use in Fraction A include thermoplastic urethanes available under the name Estanet from The B. F. Goodrich Company of Cleveland, Ohio. The amount of Fraction A in the polymer mixture will vary depending upon the composition of the polymer comprising Fraction A, the type of polymer comprising Fraction B, the desired level of moisture vapor permeability, the desired level of bonding between the film and substrate layers, and the desired film toughness. Fraction A is typically present in the film layer of the composite sheet structure of the invention in an amount ranging from 50% to 95% by weight, and more preferably from 70% to 85% by weight.

Fraction B is typically present in the film layer of the composite sheet structure of the instant invention in an amount ranging from 5% to 50% by weight, and more preferably between 15% and 30% by weight. Fraction B is preferably a homopolymer of an alpha-olefin, a copolymer or a terpolymer containing an alpha-olefin and one or more other monomers, or a block copolymer of a vinylarene and a conjugated diene. Fraction B may also be a blend of these homo-, co- and terpolymers. The selection of the compound for Fraction B is dependent on the composition of the fibrous material in the substrate 14. For example, if the substrate material is primarily polyethylene, the composition of Fraction B should contain an amount of polyethylene sufficient to make the film and substrate layers more compatible.

Where Fraction B is a homopolymer, the homopolymer preferably contains the repeating unit —(R—CH—CH$_2$)— in which R is hydrogen or an alkyl radical having between 1 and 8 carbon atoms. Preferred homopolymers according to the invention are low density polyethylene (PE-LD), linear low density polyethylene (PE-LLD), high density polyethylene (HDPE), very low density polyethylene (VLDPE) and polypropylene.

Where Fraction B is a co- or terpolymer, it preferably contains the repeating unit —(R—CH—CH$_2$)— above, with at least one further monoethylenically unsaturated monomer (aliphatic or aromatic), the following of which can be cited by way of example: vinyl acetate, styrene, and (meth)acrylic derivatives. This other monomer can represent up to 35% by weight of the olefinic copolymer, and more preferably from 1% to 10% by weight. Preferred copolymers to be used as Fraction B are copolymers of ethylene and propylene, ethylene vinyl acetate copolymers, copolymers of ethylene and acrylic derivatives (e.g., copolymers of ethylene, carbon monoxide and n-butyl acrylate, commonly known as EnBACO). copolymers of ethylenically unsaturated carboxylic acid monomers (e.g., acrylic acid, methacrylic acid, crotonic acid, etc.) or the neutralized metallic salts thereof (as found in the partially neutralized ethylene/carboxylic acid copolymers which are commonly referred to in the art as ionomers). Fraction B may also comprise terpolymers based on olefin, methyl acrylate and ethyl acrylate or even mixtures of straight chain and low density polyolefins. Where Fraction B is a block copolymer of a vinylarene and a conjugated diene, it may have the general structure A—B—A wherein the two terminal polymer blocks A comprise thermoplastic polymer blocks of vinylarenes such as polystyrene, while block B is a polymer block of selectively hydrogenated conjugated diene such as isoprene or butadiene. The proportion of the thermoplastic terminal blocks to the center elastomeric polymer block and the relative molecular weights of each of these blocks is balanced to obtain a rubber having an optimum combination of properties such that it behaves as a vulcanized rubber without requiring the actual step of vulcanization. Such compounds are commonly referred to as S-EB-S block copolymers and are available from Shell Chemical Company under the name Kraton®. Kraton® is a registered trademark of Shell Oil Company. Optionally, these block copolymers can be grafted with maleic anhydride so as to form adducts which contain 0.1% to 10% by weight, preferably 0.2% to 5%, of maleic anhydride (see U.S. Pat. No. 4,578,429).

The compatibilizer of Fraction C is typically present in the film layer of the composite sheet structure of the invention in an amount ranging from 0.1% to 15% by weight, and more preferably between 1% and 8% by weight. Preferred backbones for Fraction C include low density polyethylene (PE-LD), linear low density polyethylene (PE-LLD), high density polyethylene (HDPE), very low density polyethylene (VLDPE) and polypropylene. The reactive group of Fraction C may be a grafting monomer that is grafted to this backbone, and is or contains at least one alpha- or beta-ethylenically unsaturated carbonic acid or anhydride, or a derivative thereof. Examples of such carboxylic acids and anhydrides, which may be mono-, di- or polycarboxylic acids, are acrylic acids, methacrylic acid, maleic acid, fumaric acid, itaconic hydride, maleic anhydride and substituted maleic anhydride (e.g., dimethyl maleic anhydride). Examples of derivatives of the unsaturated acids are salts, amides, imides and esters (e.g., mono- and disodium maleate, acrylamide, maleimide and diethyl fumarate). Maleic anhydride is a preferred grafting monomer for the reactive group of Fraction C. The grafting of the polymers can be carried out in the melt state, in solution or in suspension. The melt viscosity of the grafted polymer is not restricted, however, most effective alloying is found if the melt index, measured at 2.16 kg and 190° C., is between 1 and 15 g/10 min. Such grafted polymers can be prepared as known in the art.

In addition to the above fractions, the film layer in sheet structures according to the invention may contain conventional additives, such as pigments and fillers (e.g. $TiO_2$, calcium carbonate, silicas, clay, talc) and stabilizers, such as antioxidants and ultraviolet absorbers. These additives are used for a variety of purposes, including reducing the cost of the film layer of the composite sheet structure, and altering the morphology of the film layer of the sheet structure. However, such additives have been found to reduce moisture vapor transmission through the sheet structure. It is important to maintain the amount of additive in the film at a level that does not result in a moisture vapor transmission rate for the sheet that falls outside of the range required for a particular application. The film layer may be comprised of between 0.01% and 30% of additive material, and more preferably between 0.5 and 7% of an inert filler material.

Figure 4:
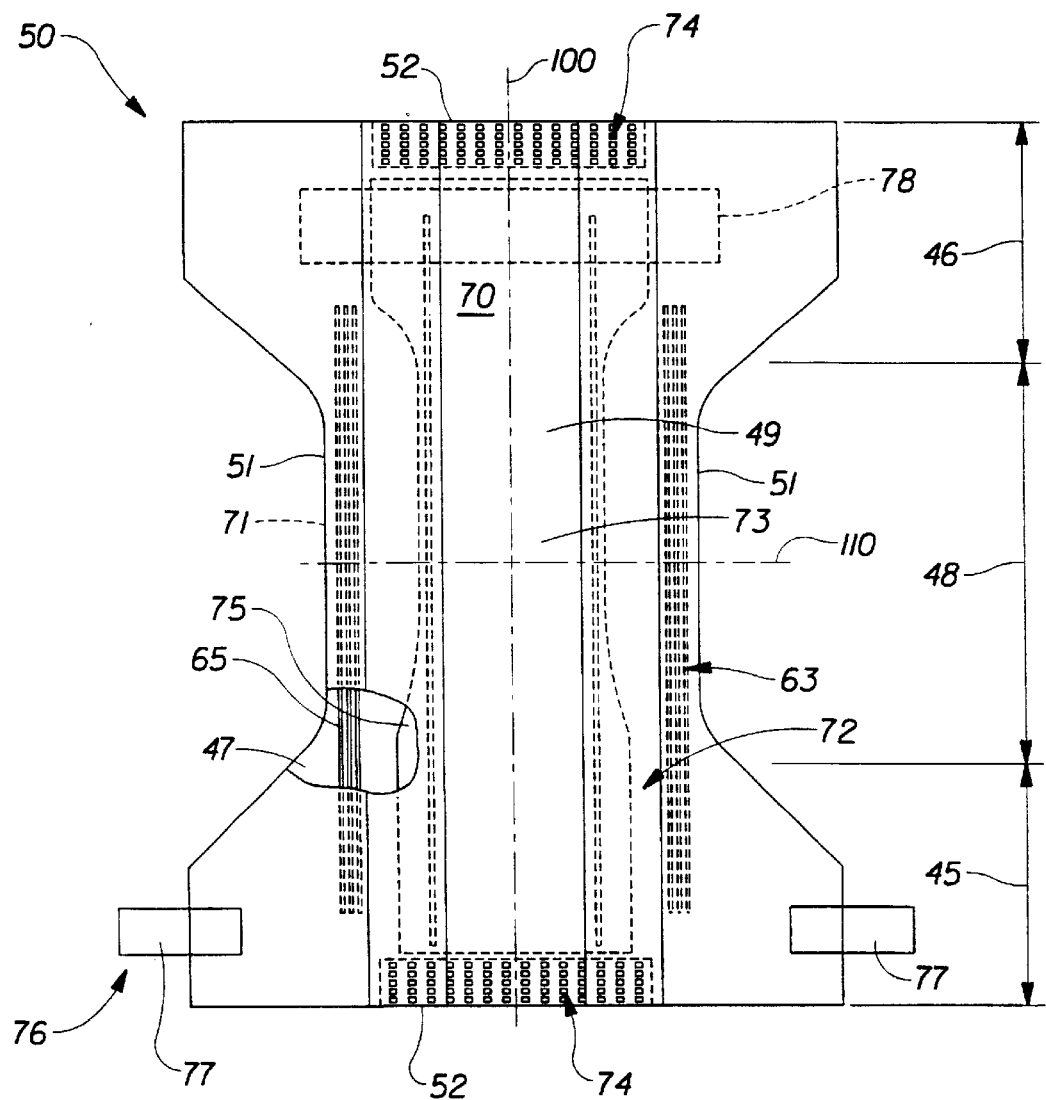
FIG. 4 is a plan view of a disposable diaper embodiment of the present invention having portions cut away to reveal underlying structure, as viewed from the inner surface of the diaper.

A preferred embodiment of an absorbent article incorporating the composite sheet of the present invention is the diaper 50, shown in FIG. 4. As used herein, the term "diaper" refers to an absorbent article generally worn by infants and incontinent persons that is worn about the lower torso of the wearer. FIG. 4 is a plan view of the diaper 50 of the present invention in its flat-out uncontracted state (i.e., with elastic induced contraction pulled out) with portions of the structure being cut-away to more clearly show the construction of the diaper 50. As shown in FIG. 4, the diaper 50 preferably comprises a containment assembly 70 comprising a topsheet 49; a backsheet 47 joined to the topsheet; and an absorbent core 75 positioned between the topsheet 49 and the backsheet 47. The absorbent core 75 has a pair of opposing longitudinal edges, an inner surface and an outer surface. The diaper preferably further comprises elastic leg features 72; elastic waist features 74; and a fastening system 76 preferably comprising a pair of securement members 77 and a landing member 78.

The diaper 50 is shown in FIG. 4 with the portion of the diaper 50 which faces the wearer, the inner surface 73, facing the viewer. The diaper 50 is shown in FIG. 4 to have an inner surface 73 (facing the viewer in FIG. 4), an outer surface 71 opposed to the inner surface 73, a rear or back waist region 45, a front waist region 46 opposed to the rear waist region 45, a crotch region 48 positioned between the rear waist region 45 and the front waist region 46, and a periphery which is defined by the outer perimeter or edges of the diaper 46 in which the longitudinal or side edges are designated 50 and the end edges are designated 52. The inner surface 73 of the diaper 50 comprises that portion of the diaper 50 which is positioned adjacent to the wearer's body during use (i.e., the inner surface 73 generally is formed by at least a portion of the topsheet 49 and other components joined to the topsheet 49). The outer surface 71 comprises that portion of the diaper 50 which is positioned away from the wearer's body (i.e., the outer surface 71 is generally formed by at least a portion of the backsheet 47 and other components joined to the backsheet 47). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 45 and the front waist region 46 extend from the end edges 52 of the periphery to the crotch region 48.

The diaper 50 also has two centerlines, a longitudinal centerline 100 and a transverse centerline 110. The term "longitudinal", as used herein, refers to a line, axis, or direction in the plane of the diaper 50 that is generally aligned with (e.g. approximately parallel with) a vertical plane which bisects a standing wearer into left and right halves when the diaper 50 is worn. The terms "transverse" and "lateral", as used herein, are interchangeable and refer to a line, axis or direction which lies within the plane of the diaper that is generally perpendicular to the longitudinal direction (which divides the wearer into front and back body halves).

Figure 5:
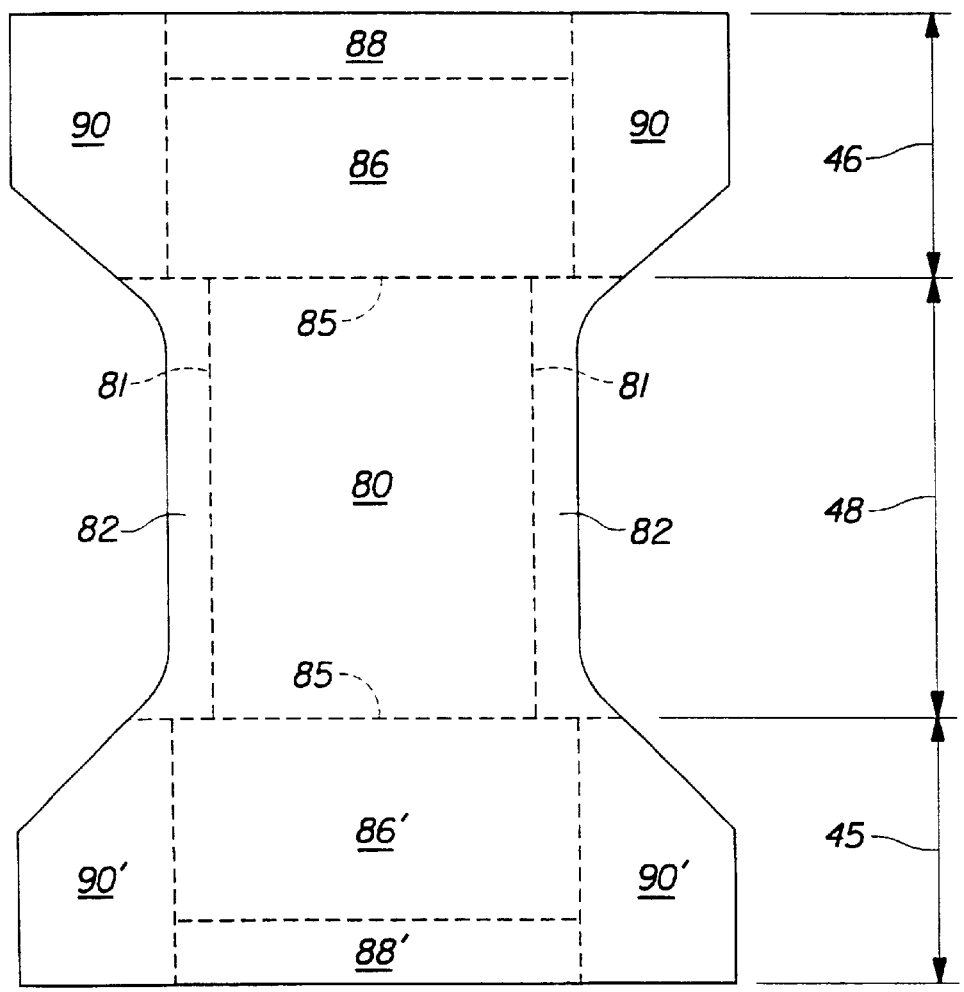
FIG. 5 is a simplified plan view of the disposable diaper of the present invention in its flat uncontracted condition showing the various panels or zones of the diaper.

FIG. 5 shows a simplified plan view of the diaper 50 of FIG. 4 depicting the various panels and their positioning with respect to each other. The term "panel" is used herein to denote an area or element of the diaper. (While a panel is typically a distinct area or element, a panel may coincide (functionally correspond) somewhat with an adjacent panel.) The diaper 50 has a crotch region 48 comprising a main panel 80 and a pair of leg panels 82; a front waist region 46 comprising a central panel comprising a medial panel 86 and a waistband panel 88, and side panels 90; and a rear waist region 45 comprising a central panel comprising a medial panel 86' and a waistband panel 88', and side panels 90'. The main panel 80 is the portion of the diaper 50 from which the other panels emanate. The absorbent core is generally positioned within the main panel 80 since exudates are typically discharged in this region of the diaper although the absorbent core will also likely extend into the medial panels 86 and 86'. A leg panel 82 extends generally laterally outwardly from and along each side edge 81 of the main panel 80. Each leg panel 82 generally forms at least a portion of the elastic leg feature. In the front waist region 46, the medial panel 86 of the central panel extends generally longitudinally outwardly from and along the lateral edge 85 of the main panel 80. The waistband panel 88 extends generally longitudinally outwardly from and along the medial panel 86. The side panels 90 each extend generally laterally outwardly from and along the central panel. In the rear waist region 44, the medial panel 86' of the central panel extends generally longitudinally outwardly from and along the lateral edge 85 of the main panel 80. The waistband panel 88' extends generally longitudinally outwardly from and along the medial panel 86'. The side panels 90' each extend generally laterally outwardly from and along the central panel.

Referring again to FIG. 4, the containment assembly 70 of the diaper 50 is shown as comprising the main body (chassis) of the diaper 50. The containment assembly 70 preferably comprises a top sheet 49, a backsheet 47 and an absorbent core 75 having a pair of opposing longitudinal edges, an inner surface, an outer surface. The inner surface of the absorbent core generally faces the body of the wearer while the outer surface generally faces away from the body of the wearer. When the absorbent article comprises a separate holder and a liner, the containment assembly 70 generally comprises the holder and the liner (i.e., the containment assembly 70 comprises one or more layers of material to define the holder while the liner comprises an absorbent composite such as a topsheet, a backsheet, and an absorbent core.) For unitary absorbent articles, the containment assembly 70 preferably comprises the topsheet 49, the backsheet 47 and the absorbent core 75 of the diaper with other features added to form the composite diaper structure.

FIG. 4 shows a preferred embodiment of the containment assembly 70 in which the topsheet 49 and the backsheet 47 have length and width dimensions generally larger than those of the absorbent core 75. The topsheet 49 and the backsheet 47 extend beyond the edges of the absorbent core 75 to thereby form the periphery of the diaper 50. While the topsheet 49, the backsheet 47, and the absorbent core 75 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; and U.S. Pat. No. 5,385,500 entitled "Absorbent Articles Providing Sustained Dynamic Fit" which issued to LaVon et al., on Oct. 25, 1994; each of which is incorporated herein by reference.

In the embodiment shown in FIG. 4, the backsheet 47 preferably comprises a continuous sheet or layer which defines the front waist region 46, the rear waist region 45, and the crotch region 48. As used herein, the term "layer" does not necessarily limit the element to a single strata of material in that a layer may actually comprise laminates or combinations of sheets or webs of the requisite types of materials. The backsheet 47 has an inner surface and an opposed outer surface. The inner surface is that portion of the backsheet 47 which is positioned adjacent the absorbent core. The outer surface of the backsheet 47 corresponds to the outer surface 71 of the diaper 50. Since the backsheet 47 preferably defines the front waist region 46, the rear waist 45, and the crotch region 48, the backsheet 47 also has corresponding regions and panels as previously defined. (For simplicity, these regions and panels are denoted in the drawings by the same reference numerals as the corresponding diaper regions and panels as shown in FIG. 5.)

In the embodiment shown in FIG. 4, the absorbent core is positioned in the main panel 80, since exudates are typically discharged in this region and extends into the medial panels 86 and 86'. In the embodiment shown in FIG. 4, the absorbent core does not extend into the leg panels 82, the waistband panels 88 and 88', or the side panels 90 and 90'. In other embodiments, the absorbent core may extend into all or some of the leg panels 82, the waistband panels 88 and 88', and the side panels 90 and 90'.

The backsheet 47 of the present invention is that portion of the diaper 50 which is generally positioned away from the wearer's skin and which prevents the exudates absorbed and contained in the absorbent core 75 from wetting articles which contact the diaper 50 such as bedsheets and undergarments. Thus, the backsheet 47 is substantially impervious to fluids (e.g., urine). In addition to being fluid impervious, the backsheet 47 is also permeable to moisture vapor. For disposable diapers, moisture vapor permeability has been found to be critical to performance especially in hot and humid conditions. When an absorbent article is positioned on a wearer, the skin is occluded by the materials making up the absorbent article. This occlusion of the skin, especially in hot and humid conditions, prevents evaporation and the resulting cooling of the occluded area. The resultant perspiration raises the relative humidity of air inside of the absorbent article resulting in less comfort for the wearer and perceived negative benefits by caregivers. In order to reduce humidity and heat buildup within the disposable diaper, it has been found that at least a portion of the backsheet 47, and more preferably the entire backsheet 47, should have a moisture vapor transmission rate of at least about 1500 $g/m^2/24$ hr., and preferably at least about 2500 $g/m^2/24$ hr, and even more preferably at least about 4000 $g/m^2/24$ hr. As discussed above, the composite sheet 10 of the present invention has an ideal moisture vapor transmission rate for use as a backsheet in a disposable absorbent article, such as the disposable diaper 50 of FIG. 4. For such an application, the composite sheet 10 is employed with the film layer 12 forming the inner or core-facing portion of the backsheet and the substrate 14 forming the outer or garment-facing portion of the backsheet.

The backsheet 47 comprised of the composite sheet 10 is preferably positioned adjacent the outer surface of the absorbent core 75 and is preferably joined thereto by any suitable attachment means known in the art for bonding such materials. For example, the backsheet 47 may be secured to the absorbent core 75 by a uniform continuous layer of adhesive, a patterned layer of adhesive, or an array of separate lines, spirals, or spots of adhesive. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference.

Alternatively, the attachment means may comprise heat bonds, pressure bonds, ultrasonic bonds, dynamic mechanical bonds, or any other suitable attachment means or combinations of these attachment means as are known in the art.

In terms of approaches to bond the composite sheet material to other components of an absorbent article, and more particularly to bond the moisture vapor permeable, liquid impermeable film layer of the composite sheet to other components, it has been observed that only certain methods of bonding will form bonds of sufficient strength to survive forces encountered in normal use particularly after the film layer has been subjected to fluid contact and has absorbed fluid. Without wishing to be bound by theory it is presently believed that the film layers of interest in accordance with the present invention provide the desired superior performance properties in terms of moisture vapor transmission due to their comparatively high moisture content under in-use conditions. This comparatively high moisture content, however, is presently believed to have negative implications on the bond strength of the bond between certain conventional hot melt adhesives and the film layer.

One approach which has proven satisfactory is to utilize a polyurethane-based adhesive in accordance with the conventional adhesive application techniques and equipment generally well known in the art, such as described above. Another approach, which is presently preferred, is to utilize the multiple layer, co-extruded film layer described above with reference to the aforementioned and incorporated U.S. Pat. No. 4,725,481 to Ostapchenko. In utilizing this multiple layer film approach, the multiple layer film structure (in a bi-layer execution) is extruded onto the fibrous substrate material with the comparatively more hydrophobic elastomer layer facing outwardly from the substrate and the comparatively more hydrophilic elastomer layer facing toward the substrate. Typically, for a given thickness the hydrophobic elastomer layer exhibits a lower MVTR performance than the hydrophilic elastomer layer due to its comparatively lower moisture content under in-use conditions. However, when employed in a comparatively thin layer, the effect of the hydrophobic lower moisture content film layer does not significantly diminish the MVTR performance of the overall composite sheet. Due to the comparatively low moisture content of the hydrophobic elastomer layer, conventional hot melt adhesives and bonding techniques may be utilized to successfully form bonds of adequate strength between the composite sheet and other components of the absorbent article even when the film has been wetted. Accordingly, by utilizing a co-extruded, multiple layer, multi-chemistry film layer a composite sheet can be provided that exhibits both the desired performance properties for the composite sheet of the present invention and can be bonded to other components of absorbent articles via conventional adhesive bonding techniques. (See Examples 36–39 below.)

Quite unexpectedly, additional performance benefits have been discovered through the use of multiple layer films in composite sheets used in constructing absorbent articles such as diaper 50. More particularly, the use of a multiple layer film comprising a three-layer structure with a hydrophobic elastomer layer on both facing surfaces surrounding a hydrophilic elastomer layer is believed to deliver improved tactile qualities when extruded onto a fibrous substrate to form a composite sheet. Again without wishing to be bound by theory, it is believed that the comparatively lower moisture content of the hydrophobic film layers results in a drier tactile impression when the fibrous substrate layer is touched or palpated, particularly when the fibrous substrate layer is comparatively thin. Such a multiple layer (tri-layer) embodiment of a composite sheet material would therefore provide both an improved bondability with conventional adhesive techniques and an improved tactile impression from the side of the fibrous substrate layer. Optionally, as discussed above, truly dual-sided configurations could be constructed analogously to FIG. 2 wherein the multiple layer/tri-layer film structure is faced on both sides with a fibrous substrate layer. Optionally, as discussed above, truly dual-sided configurations could be constructed analogously to FIG. 2 wherein the multiple layer/tri-layer film structure is faced on both sides with a fibrous substrate material to provide an enhanced tactile impression from both sides. Such an execution is believed to be particularly desirable for such applications as leg cuffs, waistbands, side panels, and other aspects of absorbent articles such as diapers where a wearer may contact both opposing surfaces of the composite sheet material.

Embodiments of the present invention are also contemplated wherein the absorbent core is not joined to the backsheet 47, and/or the topsheet 49 in order to provide greater extensibility in the front waist region 46 and the rear waist region 45.

The absorbent core 75 may be any absorbent member which is generally compressible, conformable, non-irritating to the wearer's skin, and capable of absorbing and retaining fluids such as urine and other certain body exudates. As shown in FIG. 4, the absorbent core 75 has a garment-facing side, a body-facing side, a pair of side edges, and a pair of waist edges. The absorbent core 75 may be manufactured in a wide variety of sizes and shapes (e.g., rectangular, hourglass, "T"-shaped, asymmetric, etc.) and from a wide variety of fluid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 75 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 75 may also be varied to accommodate wearers ranging from infants through adults. However, the total absorbent capacity of the absorbent core 75 should be compatible with the design loading and the intended use of the diaper 50.

One embodiment of the diaper 50 has an asymmetric, modified T-shaped absorbent core 75 having ears in the front waist region but a generally rectangular shape in the rear waist region. Exemplary absorbent structures for use as the absorbent core 75 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The topsheet 49 is preferably positioned adjacent the inner surface of the absorbent core 75 and is preferably joined thereto and to the backsheet 47 by attachment means (not shown) such as those described above with respect to joining the backsheet 49 to the absorbent core 47. In a preferred embodiment of the present invention, the topsheet 49 and the backsheet 47 are joined directly to each other in the diaper periphery and are indirectly joined together by directly joining them to the absorbent core 75 by any suitable means.

The topsheet 49 is preferably compliant, soft feeling, and non-irritating to the wearer's skin. Further, the topsheet 49 is preferably fluid pervious permitting fluids (e.g., urine) to readily penetrate through its thickness. A suitable topsheet 49 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 49 is preferably made of a hydrophobic material to isolate the wearer's skin from fluids which have passed through the topsheet 49 and are contained in the absorbent core 75 (i.e. to prevent rewet). If the topsheet 49 is made of a hydrophobic material, at least the upper surface of the topsheet 49 is treated to be hydrophilic so that fluids will transfer through the topsheet more rapidly. This diminishes the likelihood that body exudates will flow off the topsheet 49 rather than being drawn through the topsheet 49 and being absorbed by the absorbent core 75. The topsheet 49 can be rendered hydrophilic by treating it with a surfactant. Suitable methods for treating the topsheet 49 with a surfactant include spraying the topsheet 49 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein. As mentioned in the background discussion above, such hydrophilic materials tend to reduce the surface tension of bodily fluids discharged into an absorbent article, which increases the likelihood of liquid seepage if there are pores or pinholes in the backsheet of the article.

An alternative preferred topsheet comprises an apertured formed film. Apertured formed films are preferred for the topsheet because they are pervious to body exudates and yet non-absorbent and have a reduced tendency to allow fluids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference.

It may also be desirable to provide the disposable absorbent article of the present invention with extensibility or elasticity in all or a portion of the side panels 90. (As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 90 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 90 further provide more effective application of the diaper 50 since even if the diaperer pulls one side panel 90 farther than the other during the application (asymmetrically), the diaper 50 will "self-adjust" during wear. While the extensible side panels 90 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992; each of which are incorporated herein by reference.

The extensible side panels, or any other elements of the diaper 50 in which extensibility or elasticity is desirable such as the waistbands may comprise materials that have been "prestrained", or "mechanically prestrained" (i.e., subjected to some degree of localized pattern mechanical stretching to permanently elongate the material), or structural elastic-like webs, as described in U.S. Pat. No. 5,518,801 issued to Chappell et al. on May 21, 1996. The materials may be prestrained using deep embossing techniques as are known in the art. Alternatively, the materials may be prestrained by directing the material through an incremental mechanical stretching system as described in U.S. Pat. No. 5,330,458 issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively;

U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

The diaper 50 preferably further comprises elastic leg features 72 for providing improved containment of fluids and other body exudates. Each elastic leg feature 72 may comprise several different embodiments for reducing the leakage of body exudates in the leg panels 82 (the elastic leg feature can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free fluids within the garment. Each of these patents are incorporated herein by reference.

While each elastic leg feature 72 may be configured so as to be similar to any of the leg bands, side flaps, barrier cuffs, or elastic cuffs described above, it is preferred that each elastic leg feature 72 comprise at least an inner barrier cuff comprising a barrier flap and a spacing element such as described in the above-referenced U.S. Pat. No. 4,909,803. In a preferred embodiment, the elastic leg feature 72 additionally comprises an elastic gasketing cuff 63 with one or more elastic strands 65, positioned outboard of the barrier cuff such as described in the above-referred U.S. Pat. No. 4,695,278.

The diaper 50 preferably further comprises an elastic waist feature 74 that provides improved fit and containment. The elastic waist feature 74 is that portion or zone of the diaper 50 which is intended to elastically expand and contract to dynamically fit the wearer's waist. The elastic waist feature 74 preferably extends longitudinally outwardly from at least one of the waist edges of the absorbent core 75 and generally forms at least a portion of the end edge of the diaper 50. Disposable diapers are generally constructed so as to have two elasticized waistbands, one positioned in the rear waist region and one positioned in the front waist region, although diapers can be constructed with a single elasticized waistband. Further, while the elastic waist feature 74 or any of its constituent elements can comprise a separate element affixed to the diaper 50, the elastic waist feature 74 may be constructed as an extension of other elements of the diaper such as the backsheet 47 or the topsheet 49, preferably both the backsheet 47 and the topsheet 49. Embodiments are also contemplated wherein the elastic waist feature 74 comprises apertures, as described above, to provide breathability in the waist regions. The elastic waist feature 74 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference.

The diaper 50 also comprises a fastening system 76 which forms a side closure which maintains the rear waist region 45 and the front waist region 46 in an overlapping configuration such that lateral tensions are maintained around the circumference of the diaper to maintain the diaper on the wearer. Exemplary fastening systems are disclosed in U.S. Pat. No. 3,848,594 issued to Buell on Nov. 19, 1974; U.S. Pat. No. 4,662,875 issued to Hirotsu and Robertson on May 5, 1987; U.S. Pat. No. 4,869,724 issued to Scripps on Sep. 26, 1989; U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; and U.S. Pat. No. 5,326,612 entitled "Nonwoven Female Component For Refastenable Fastening Device And Method of Making the Same" issued to David J. K. Goulait on Jul. 5, 1994. Each of these patents are incorporated herein by reference.

Figure 6:
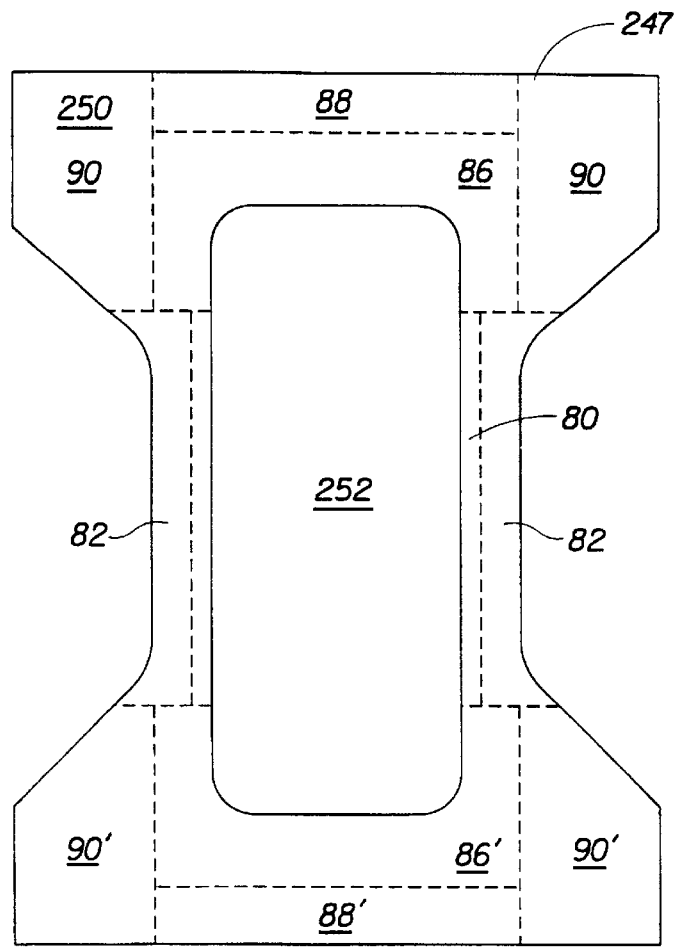
FIG. 6 is a plan view of another embodiment of a diaper backsheet of the present invention.

FIG. 6 shows a plan view of an alternative embodiment of the diaper backsheet of the present invention, with the portion of the backsheet positioned adjacent to the absorbent core facing the viewer. As shown in FIG. 6, the backsheet 247 comprises two layers 250 and 252. Layers 250 and 252 may be secured together by any suitable attachment means such as those described above. In this embodiment, layer 250 forms the outer surface of the diaper and layer 252 is positioned adjacent to the absorbent core. Since layer 250 is that portion of the backsheet 247 which will come into contact with the wearer's skin, layer 250 is preferably soft and comprises a nonwoven web. In addition to being soft, layer 250 is preferably moisture vapor permeable. Layer 250 preferably exhibits a moisture vapor transmission rate, of at least about 2000 $g/m^2/24$ hr., more preferably at least about 2500 $g/m^2/24$ hr. Since layer 250 does not need to prevent leakage of exudates absorbed and contained within the absorbent core, selection of materials that provide the desired softness and breathability is quite extensive. Suitable materials include, but are not limited to, nonwoven webs such as spunbond webs, meltblown webs, carded webs and the like. The nonwoven webs for layer 250 may comprise synthetic fibers, natural fibers, multi-component fibers such as bi-component fibers, or mixtures and blends thereof.

Layer 252 is the portion of the backsheet 247 which will prevent the exudates absorbed and contained in the absorbent core from wetting articles which contact the diaper. In order to protect the user against unwanted leakage of exudates absorbed and contained within the absorbent core layer 252 should have width and length dimensions greater than those of the absorbent core. If layer 252 is not large enough exudates absorbed and contained in the absorbent core may find their way through the outer layer 250 during normal usage conditions. In the embodiment shown in FIG. 7, the absorbent core is preferably positioned in the main panel 80 and extends into the medial panels 86 and 86'. Accordingly, layer 252 is positioned within the main panel 80 and extends into the medial panels 86 and 86'. Layer 252 has length and width dimensions at least as large as those of the absorbent core and preferably greater than those of the absorbent core. If desired, layer 252 may extend beyond the main panel 80 and the medial panels 86 and 86' to into the leg panels 82, the waistband panels 88 and 88', and the side panels 90 and 90'. In addition, layer 252 may extend laterally and longitudinally outwardly from the main panel 80 to form portions of the periphery of the disposable diaper.

While layer 250 provides a substantial amount of moisture vapor permeability for the diaper, layer 252 should also be moisture vapor permeable in order to provide additional comfort for the wearer. In the embodiment of the invention shown in FIG. 6, layer 252 is comprised of the composite sheet 10 described above.

While a presently preferred embodiment of an absorbent article such as diaper 50 according to the present invention utilizes a composite sheet 10 according to the present invention for substantially the full extent of the backsheet 47, it is to be understood that the absorbent articles are in no way limited to such an embodiment. For example, a backsheet could be constructed from multiple backsheet elements having similar or diverse properties and constructions as described above with regard to FIG. 6. One such approach would be to form a backsheet with an external facing surface of a unitary or composite nonwoven layer as a substrate with the film layer comprising only the region of the backsheet where fluid imperviousness is desired, such as, for example, the region corresponding to the region 252 depicted in FIG. 6.

Moreover, it may also be desirable for certain applications to reverse the orientation of the layers 250 and 252 of FIG. 6 so as to place the film layer on the external or garment-facing side of the backsheet and the fibrous substrate layer on the internal or absorbent-core-facing side of the backsheet. It may also likewise be desirable to utilize the composite sheet 10 in the dual-sided embodiment of FIG. 2 wherein both sides of the backsheet would be faced with a fibrous layer. All such variations are contemplated as being within the scope of the present invention. Moreover, depending upon the specific application, the properties provided by the composite sheets of the present invention may also be employed to great advantage in other regions of the absorbent article besides the central portion of the backsheet which overlies the absorbent core structure. For example, the desirable fluid-impervious, moisture-vapor-pervious properties of the composite sheet also provide desirable attributes for peripheral portions of the absorbent article which extend laterally outwardly from the marginal edges of the absorbent core such as the side panels 90, 90' depicted in FIG. 5. Other such "peripheral portions" of the absorbent article for which such attributes may be desirable are in the vicinity of the leg panels 82 including but not limited to various bands, cuffs, and flaps.

Likewise, while much of the foregoing discussion as focused upon the representative absorbent article in the form of diaper 50, it is to be understood that the materials and principles of the present invention are equally applicable to other absorbent articles such as incontinence briefs, incontinence undergarments, diaper holders and liners, feminine hygiene products (sanitary napkins, pantiliners, etc.), training pants, pull-on garments, and the like wherein the materials of the present invention may be employed advantageously. By way of illustration, a backsheet of a sanitary napkin according to the present invention could be formed from a composite sheet of the present invention, as could peripheral portions of a sanitary napkin such as wings or side flaps.

After manufacture of the composite sheet 10, and either before or after the sheet's incorporation into an absorbent article, it may be desirable to subject the sheet to a post-formation mechanical process such as creping, straining/activation by rolling with corrugated rolls, or otherwise. One such representative process is described in detail in U.S. Pat. No. 5,518,801 to Chappell et al., the disclosure of which is hereby incorporated herein by reference, The following non-limiting examples are intended to illustrate the product and process of the invention and not to limit the invention in any manner.

EXAMPLES

In the description above and in the non-limiting examples that follow, the following test methods were employed to determine various reported characteristics and properties. ASTM refers to the American Society for Testing and Materials, TAPPI refers to the Technical Association of Pulp and Paper Industry, and ISO refers to the International Organization for Standardization.

Basis weight was determined by ASTM D-3776 which is hereby incorporated by reference, and is reported in g/m$^2$.

Composite Sheet Thickness was determined by ASTM method D 1777-64, which is hereby incorporated by reference, and is reported in microns.

Film Thickness, is reported in microns, and was determined as follows:

$$\text{Film thickness} = \frac{(\text{composite sheet sample weight}) - (\text{substrate basis weight})(\text{sample area})}{(\text{sample area})(\text{density of film material})}$$

Tensile strength was determined by ASTM D 1682, Section 19, which is hereby incorporated by reference, with the following modifications. In the test a 2.54 cm by 20.32 cm (1 inch by 8 inch) sample was clamped at opposite ends of the sample. The clamps were attached 12.7 cm (5 in) from each other on the sample. The sample was pulled steadily at a speed of 5.08 cm/min (2 in/min) until the sample broke. The force at break was recorded in Newtons/cm as the breaking tensile strength.

Elongation to Break of a sheet is a measure of the amount a sheet stretches prior to failure (breaking)in a strip tensile test. A 1.0 inch (2.54 cm) wide sample is mounted in the clamps—set 5.0 inches (12.7 cm) apart—of a constant rate of extension tensile testing machine such as an Instron table model tester. A continuously increasing load is applied to the sample at a crosshead speed of 2.0 in/min (5.08 cm/min) until failure. The measurement is given in percentage of stretch prior to failure. The test generally follows ASTM D 1682-64.

Peel strength is measured according to a test that generally follows the method of ASTM D 2724-87, which is hereby incorporated by reference. The test was performed under two different conditions, both of which used a constant rate of extension tensile testing machine such as an Instron table model tester.

According to what we define as test Condition A, which was used in Examples 1–17 and in discussion portion of the specification, a 2.54 cm (1.0 in) by 20.32 cm (8.0 in) sample is delaminated approximately 3.18 cm (1.25 in) by inserting a pick into the cross-section of the sample to initiate a separation and then delaminated by hand. The delaminated sample faces are mounted in the clamps of the tester which are set 2.54 cm (1.0 in) apart. The tester is started and run at a cross-head speed of 5.08 cm/min (2.0 in/min). The computer starts picking up readings after the slack is removed in about 1.27 cm (0.5 in) of crosshead travel. The sample is delaminated for about 15.24 cm (6 in) during which approximately 3000 readings are taken and averaged. The average delamination strength is given in N/cm. A suitable method for initiating the peel is to dip the end of a sample in isopropyl alcohol to swell the sample, begin peeling by hand, and then remove and discard the portion of the sample contacted with the alcohol before measuring peel strength.

According to what we define as test Condition B, which was used in Examples 18–34, the method to test Condition A is used except that the samples are 15 cm (6 in) long, a crosshead speed of 10 in/min is used, peel is initiated by hand rather than with a pick, and delamination strength was recorded from the average indicated on the recording chart.

Moisture Vapor Transmission Rate (MVTR) was determined by one of two test methods. The first method used follows ASTM E96-B, which is hereby incorporated by reference, and is reported in $g/m^2/24$ hrs.

The second method is referred to as the dessicant method for measuring moisture vapor transmission rate as set forth below. Briefly summarizing this method, a known amount of desiccant ($CaCl_2$) is put into a flanged "cup" like container. The sample material is placed on the top of the container and held securely by a retaining ring and gasket. The assembly is then weighed and recorded as the initial weight. The assembly is placed in a constant temperature (40° C.) and humidity (75% RH) chamber for five (5) hours. The assembly is then removed from the chamber, sealed to prevent further moisture intake, and allowed to equilibrate for at least 30 minutes at the temperature of the room where the balance is located. The amount of moisture absorbed by the $CaCl_2$ is determined gravimetrically and used to estimate the moisture vapor transmission rate (MVTR) of the sample by weighing the assembly and recording the final weight. The moisture vapor transmission rate (MVTR) is calculated and expressed in $g/m^2/24$ hr. using the formula below. A reference sample, of established permeability, is used as a positive control for each batch of samples. Samples are assayed in triplicate. The reported MVTR is the average of the triplicate analyses, rounded to the nearest 100. The significance of differences in MVTR values found for different samples can be estimated based on the standard deviation of the triplicate assays for each sample.

Suitable Analytical Balances for performing the measurements include a Mettler AE240 or equivalent (300 g capacity) or a Sartorius 2254S0002 or equivalent (1000 g capacity). A suitable sample holding assembly comprises a cup and retaining ring machined from Delrin® (such as that available from McMaster-Carr Catalog #8572K34) with a gasket made of GC Septum Material (Alltech catalog #6528). The dessicant comprises $CaCl_2$ for U-tubes, available from Wako Pure Chemical Industries, Ltd., Richmond, Va. Product #030-00525. The plastic food wrap comprises Saran Wrap. available from Dow Chemical Company, or equivalent.

The $CaCl_2$ can be used directly from a sealed bottle as long as the size of the lumps is such that they do not pass through a No. 10 sieve. Usually the top two-thirds of the bottle does not have to be seived. However, the bottom third contains fines that should be removed by sieving. The $CaCl_2$ can be used from a closed container without drying. It can be dried at 200° C. for 4 hours if required.

Exxon Exxaire microporous material, Catalog # XBF-100W, is used as the Reference Standard Material. Triplicate samples should be prepared and analyzed along with each set of test samples as described below.

Representative samples should be obtained from the materials to be tested. Ideally, these samples should be taken from different areas of the material so as to represent any variations present. Three samples of each material are needed for this analysis.

Samples should be cut into rectangular pieces approximately 1.5"×2.5". If the samples are not uniform, clearly mark the area for which breathability is to be evaluated. If the samples are not bidirectional, clearly mark the side that is to be exposed to high humidity. For samples used in diapers and catamenials, this is usually the side that contacts the skin.

To begin a test session, (1) weigh 15.0±0.02 grams of $CaCl_2$ and place in the MVTR cup. Gently tap the cup 10 times on the bench top to distribute and lightly pack the $CaCl_2$. The $CaCl_2$ should be level and about 1 cm from the top of the cup. Then (2) place the sample, with the high humidity side up (if required), over the opening in the top of the cup. Make sure that the sample overlaps the opening so that a good seal will be obtained. Next, (3) place the gasket material and the retaining ring on the top of the cup, aligning the screw holes and checking to make sure that the sample has not moved. Tighten the screws to securely fasten the retaining ring and seal the sample to the top of the cup. Care should be taken to not overtighten the screws as this leads to distortion of some samples. If distortion of the sample occurs, loosen the screws and tighten again. Then (4) weigh the MVTR cup assembled in step 3. Record this weight as the initial weight.

After weighing the assembly, (5) place the sample in the CT/CH chamber for 5.0 hours (to the nearest minute). When the time has elapsed, (6) remove the sample from the CT/CH chamber, tightly cover it with plastic wrap secured by a rubber band. Record the time of sample removal to within the nearest minute. Allow samples to equilibrate for at least 30 minutes at the temperature of the room where the balance is located. After equilibration, (7) remove the Saran wrap and weigh the cup. Record this weight as the final weight.

The MVTR is then calculated in units of g $H_2O/24$ hr/m2 using the formula:

$$MVTR = \frac{(\text{final weight} - \text{initial weight}) \times 24.0}{\text{area of sample in meters} \times 5.0 \text{ (time in chamber)}}$$

where:
24.0 is used to convert the data to the 24 hour basis;
the area of sample is equal to the open area of the mouth of the cup; and
5.0 is the duration of the test in hours Calculate the average MVTR for each set of triplicate samples and the reference standard. Round the average MVTR for the reference standard to the nearest 100. If the MVTR for the reference standard is in the range of 4000 to 4600, it is in the acceptable quality control range and the results for that day can be reported. Round the average MVTR for each sample set to the nearest 100. Report this value as the MVTR for the sample of material. Steps 1 through 7 are repeated for the triplicate analyses of each sample and the reference standard. Typically, multiple samples are processed in parallel.

Figure 7:
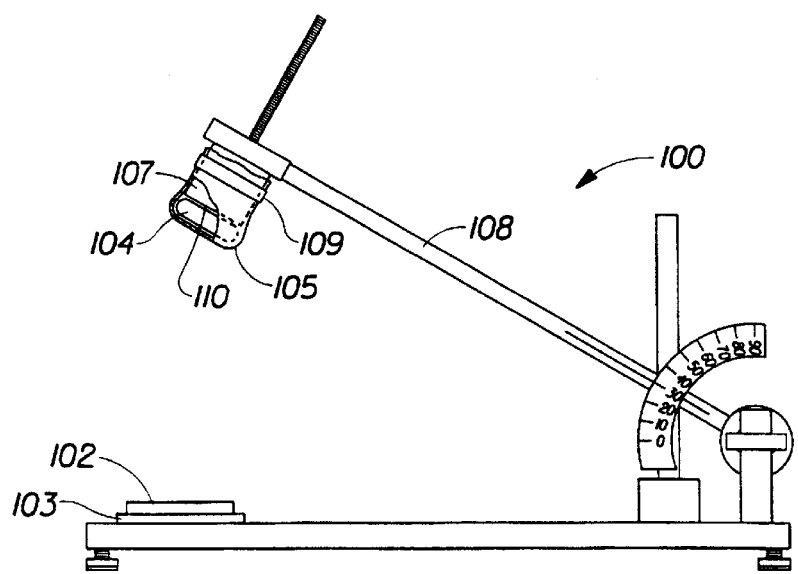
FIG. 7 is a simplified illustration of an apparatus used for measuring dynamic fluid transmission of a sheet material.

Dynamic Fluid Transmission is measured with the apparatus 100 shown in FIG. 7. According to this test, an absorption material 102 weighed to the nearest 0.0001 gram is placed directly on top of the energy absorbing impact pad 103. The absorption material 102 may comprise a No. 2 filter paper available from Whatman Laboratory Division, Distributed by VWR Scientific of Cleveland, Ohio. The absorption material should be able to absorb and retain simulated urine which passes through the sheet material being tested. The energy absorbing impact pad 103 is a carbon black filled cross linked rubber foam. The 5 inch by 5 inch square impact pad has a density of 0.1132 $g/cm^3$ and athickness of 0.3125 inches. The impact pad 103 has a Durometer Value of A/30/15 according to ASTM 2240-91. A circular absorbent core material 104 measuring 0.0635 meters (2.5 inches) in diameter is weighed. The absorbent core material may comprise individualized, crosslinked wood pulp cellulosic fibers as described in U.S. Pat. No. 5,137,537 issued to Herron et al. on Aug. 11, 1992. The absorbent core material should be able to hold a sufficient amount of simulated urine, e.g., at least about ten times its dry weight. The absorbent core has a basis weight of about 228 g/m². The absorbent core material is then is loaded with simulated urine to about ten (10) times its dry weight. The simulated urine is an aqueous composition, maintained at 37° C., and comprised of the following components dissolved in distilled water: 2.0 g/L KCl; 2.0 g/L Na$_2$SO$_4$; 0.85 g/L (NH$_4$)H$_2$PO$_4$; 0.15 g/L (NH$_4$)$_2$H$_2$PO$_4$; 0.19 g/L CaCl$_2$; and 0.23 g/L MgCl$_2$.

A section of the backsheet material 105 to be tested is placed face down with the outside surface on a clean and dry tabletop. The loaded core material 104 is placed directly in the center of the backsheet material 105. The backsheet/core arrangement is then secured to the impact portion 107 of the impact arm 108 with a rubber band 109. The backsheet/core arrangement is positioned such that the core 104 is adjacent the bottom surface 110 of the impact portion 107. The impact arm 108 is raised to a desired impact angle to provide the desired impact energy. The impact arm 108 is dropped and the impact arm 108 is then immediately (about 1 second after impact) raised and the filter paper 102 is removed and placed on a digital scale. The mass of the wet filter paper is then recorded at the three minute mark. The dynamic fluid transmission value (DFTV) is calculated and expressed in g/m² using the following formula:

$$DFTV = \frac{\text{mass of the wet filter paper (grams)} - \text{mass of the dry filter paper (grams)}}{\text{impact area (m}^2\text{)}}$$

The impact area, expressed in m², is the area of the bottom surface 110 of the impact portion 107. The impact area is 0.00317 m². The absorbent core material 104 should have an area slightly larger than that of the impact area of the surface 110.

Gurley Hill Porosity is a measure of the barrier strength of the sheet material for gaseous materials. In particular, it is a measure of how long it takes for a volume of gas to pass through an area of material wherein a certain pressure gradient exists. Gurley-Hill porosity is measured in accordance with TAPPI T-460 om-88 using a Lorentzen & Wettre Model 121D Densometer. This test measures the time of which 100 cubic centimeters of air is pushed through a one inch diameter sample under a pressure of approximately 4.9 inches of water. The result is expressed in seconds and is usually referred to as Gurley Seconds.

Microbial Barrier for Sterile Packaging is measured according to ISO 11607 which states under section 4.2.3.2 that a material that is impermeable to air for one hour (according to an air porosity test) satisfies the standard's microbial barrier requirements. With regard to porous materials, section 4.2.3.3 of ISO 11607 states that there is no universally applicable method of demonstrating microbial barrier properties in porous materials, but notes that the microbial barrier properties of porous materials is typically conducted by challenging samples with an aerosol of bacterial spores or particulates under a set of test conditions which specify the flowrate through the material, microbial challenge to the sample, and duration of the test. One such recognized test is ASTM F 1608-95.

Liquid Moisture Seepage is detected using a solution of 70 parts isopropyl alcohol, 30 parts water and 1 part red dye food color. According to this test, a sheet of a white absorbent blotting material measuring about 89 cm by 61 cm (35 in by 24 in) is placed on a flat surface and covered with a test sample of the same dimensions with the substrate side of the sample facing up. A 250 ml portion of the solution is poured on top of the test sample and covered with a template measuring about 46¾ cm by 46¾ cm (18 in by 18 in). A 4.5 kg (10 lb) weight is placed on top of the template for 10 minutes afterwhich the weight, template and test sample are removed from the white blotting paper. The paper is then inspected for ink spots to determine whether seepage occurred.

Example 1

A composition was prepared by dry blending 86% by weight of a copolyether ester thermoplastic elastomer (Hytrel® 4778 obtained from DuPont) with 4% by weight of a UV stabilizer concentrate (Hytrel® 20UV, obtained from DuPont), 4% by weight of a heat stabilizer concentrate (Hytrel® 30HS obtained from DuPont), and 6% by weight of a maleic anhydride modified polyolefin copolymer (Fusabond® 373 obtained from DuPont Canada). Fusabond® is a registered trademark of DuPont Canada. The composition was fed to a melt extrusion coating line including a single screw extruder with an attached mixing head. The screw extruder was made by Egan Division of Davis-Standard Corporation. The heating zones of the extruder heat the polymer to a temperature above its melting point. The melted polymer mixture was fed to a film die with a width of about 90 cm that was maintained at about 220° C. The polymer was laminated onto a corona treated nonwoven polypropylene textile material (Typar® thermobonded polypropylene obtained from DuPont) at a line speed of 18.3 m/min. The polymer melt and nonwoven textile material were passed through a pair of nip rolls (one rubber faced roll against the nonwoven textile material and one steel faced roll against the polymer melt). The resulting laminate had a coating thickness of about 25 microns and peel strength values of 0.063 N/cm in the machine direction (MD) and 0.032 N/cm in the cross direction (CD) and an MVTR value of 700 g/m²/24 hr (by method ASTM E96-B).

Example 2

The Typar® nonwoven fabric of Example 1 was replaced with a nonwoven polyester (compatible with copolyether ester polymers) fabric (obtained from Freudenberg, Germany) and the resulting laminate had peel strength values of 0.88 N/cm (MD) and 1.06 N/cm (CD) and an MVTR value of 750 g/m²/24 hr (by method ASTM E96-B).

Example 3

A composition was prepared by dry blending 70% by weight of a copolyether ester thermoplastic elastomer (Hytrel® 8206 obtained from DuPont) with 4% by weight UV stabilizer (Hytrel® 20UV), 4% by weight heat stabilizer (Hytrel® 30HS), 8% by weight of a maleic anhydride modified polyolefin copolymer (Fusabond® 373) and 14% by weight of a polypropylene polymer resin (PF331 obtained from Montell Polyolefins, Wilmington, Del.). The blend was extruded under the same conditions as described in Example 1 and melt laminated to the same Typar® nonwoven fabric described in Comparative Example 2. The resulting laminate had a coating thickness of about 25 microns and peel strength values of 0.26 N/cm (MD) and 0.18 g/cm (CD) and an MVTR of 800 g/m²/24 hr (by method ASTM E96-B).

Example 4

A composition was prepared by dry blending 80% by weight of a copolyether ester thermoplastic elastomer (Hytrel® 8206) with 9.3% by weight polypropylene resin (PF331 obtained from Montell Polyolefins, Wilmington, Del.), 4.7% by weight PE-LLD (Novapol 8111) obtained from Novacor Chemicals Inc., Leominster, Mass.), 4.7% by weight of a HDPE containing 30% by weight of 1 micron particle size $CaCO_3$ (Zemid™ 610 obtained from DuPont Canada, Mississauga, Ontario) and 1.3% by weight of a maleic anhydride modified polyolefin copolymer (Fusabond® MD353D). Zemid™ is a trademark of DuPont Canada. The blend was extruded under the same conditions as described in Example 1 at a line speed of 14 m/min and melt laminated to a corona treated, spunbonded, HDPE nonwoven fabric made by Corovin GMBH, of Peine, Germany. The resulting laminate had a coating thickness of about 31 microns, a peel strength of 0.64 N/cm, a tensile strength of 9.1 N/cm (MD) and 3.6 N/cm(CD), and an MVTR of 907 $g/m^2/24$ hr (by method ASTM E96-B).

Example 5

Example 4 was repeated at a line speed of 23 m/min., resulting in laminate that had a coating thickness of about 20 microns and peel strength 0.18 N/cm and an MVTR of 1011 $g/m^2/24$ hr (by method ASTM E96-B).

Example 6

A composition was prepared by dry blending 50% by weight of a copolyether ester thermoplastic elastomer (Hytrel® 8206) with 33% by weight of another copolyether ester thermoplastic elastomer (Hytrel® G3548W obtained from DuPont), 8.0% by weight polypropylene (PF331), 2.6% by weight PE-LLD (Novapol 8111), 5.4% by weight of a HDPE containing 30% by weight of 1 micron particle size $CaCO_3$ (Zemid™ 610) and 1.0% by weight of a maleic anhydride modified polyolefin copolymer (Fusabond® MD353D). The blend was extruded under the same conditions as described in Example 1 at a line speed of about 24 m/min and was melt laminated to the HDPE nonwoven fabric used in Example 4. The resulting laminate had a coating thickness of about 20 microns and peel strength values of 0.09 N/cm and an MVTR of 1159 $g/m^2/24$ hr (by method ASTM E96-B).

Example 7

A composition was prepared by dry blending 50% by weight of a copolyether ester thermoplastic elastomer (Hytrel® 8206) with 31% by weight of another copolyether ester thermoplastic elastomer (Hytrel® 8171 obtained from DuPont), 8.9% by weight polypropylene (Fina 3365 obtained from Fina Oil and Chemical of Dallas, Tex.), 2.9% by weight PE-LLD (Novapol 8111), 6.1% by weight of 1 micron particle size $CaCO_3$ (Zemid™ 610), and 1.1% by weight of a maleic anhydride modified polyolefin copolymer (Fusabond® MD353D). The blend was extruded onto a corona treated, spunbonded, polyethylene nonwoven fabric made by Polybond of Waynesboro, Va. and adhered to the nonwoven via a vacuum process. The resulting laminate had a coating thickness of about 15 microns and a peel strength of 0.05 N/cm and an MVTR of 1409 $g/m^2/24$ hr (by method ASTM E96-B).

Examples 8–17

The film compositions described below were prepared by dry blending two copolyether ester thermoplastic elastomers, either an anhydride modified polypropylene or an anhydride modified ethylene vinyl acetate, and titanium dioxide. The individual components in the film compositions were as follows:

Hytrel® 8206 copolyether ester thermoplastic elastomer sold by DuPont, and having a melting point of 200° C., a vicat softening temperature of 151° C., and a shore hardness of 45D.

Hytrel® 8171 copolyether ester thermoplastic elastomer sold by DuPont, and having a melting point of 150° C., a vicat softening temperature of 76° C., and a shore hardness of 32D.

Bynel® 50E561 anhydride modified polypropylene sold by DuPont, and having a melting temperature of 141° C., and a vicat softening temperature of 109° C.

Bynel® 50E555 anhydride modified polypropylene sold by DuPont, and having a melting temperature of 166° C., and a vicat softening temperature of 144° C.

Bynel® 3860 anhydride modified ethylene vinyl acetate sold by DuPont, and having a melting temperature of 74° C., and a vicat softening temperature of 48° C.

$TiO_2$ Concentrate was a concentrate of 50% by weight particulate titanium dioxide pigment in high density polyethylene.

The film compositions used in Examples 8–17 had the following compositions:

|  | Film Composition | | | | |
| --- | --- | --- | --- | --- | --- |
|  | A | B | C | D | E |
| Hytrel ® 8206 | 49% | 49% | 40% | 41% | 34% |
| Hytrel ® 8171 | 32% | 32% | 40% | 43% | 50% |
| Bynel ® 50E561 | 13% | — | — | — | — |
| Bynel ® 50E555 | — | 13% | 14% | — | — |
| Bynel ® 3860 | — | — | — | 10% | 10% |
| $TiO_2$ Concentrate | 6% | 6% | 6% | 6% | 6% |

The compositions were each fed to a melt extrusion coating line including a single screw extruder with an attached mixing head. The screw extruder was made by Egan Division of Davis-Standard Corporation. The compositions were fed to the extruder where they reached a temperature of about 263° C. and a pressure of 3827 kPa. The melts were fed to a film die with a width of about 80 cm that was maintained at about 220° C.

The melted polymer compositions were laminated onto sheets of carded polypropylene staple fiber, with fiber lengths generally ranging between 2.5 cm and 7.5 cm, that had been airlayed and thermal bonded. The polypropylene fiber sheet had a basis weight of 0.0305 $kg/m^2$ (0.9 $oz/yd^2$), a tensile strength of 8.3 N/cm (4.73 lb/in) in the machine direction and 1.5 N/cm (0.86 lb/in) in the cross direction, and an elongation of 73% in the machine direction and 95% in the cross direction. The polypropylene fiber sheet was spaced 24.1 cm (9.5 in) from the opening of the die and the sheet moved at a line speed of 32 m/min during lamination. The polymer melt and polypropylene fiber sheet were passed through a pair of nip rolls (one metal faced roll against the fibrous sheet material and one rubber faced roll against the polymer melt). The metal roll was maintained at about 43.3° C. (110° F.) by water cooling. Air cylinders at a pressure of 414 kPa (60 psi) were used to press the rolls together. The resulting composite sheets had the properties set forth in Table 1 below.

TABLE I

| | Example | | | | | | | | | |
|---|---|---|---|---|---|---|---|---|---|---|
| | 8 | 9 | 10 | 11 | 12 | 13 | 14 | 15 | 16 | 17 |
| Film Composition | A | A | B | B | C | C | D | D | E | E |
| Film Thickness (micron) | 20 | 25 | 20 | 25 | 20 | 25 | 20 | 25 | 20 | 25 |
| Composite Thickness (mm) | 165 | 183 | 173 | 170 | 170 | 160 | 155 | 155 | 150 | 160 |
| MVTR (Desiccant Method) (g/m$^2$/day) | 3418 | 3051 | 3486 | 3536 | 3651 | 3346 | 4246 | 3489 | 3444 | 3255 |
| Dynamic Impact (g/m$^2$ @ 2400 J/m$^2$) | 0.36 | 0.31 | 0.28 | 0.37 | 0.16 | 0.04 | 0.12 | 0 | 0 | 0 |
| Peel Strength (N/cm) | | | | | | | | | | |
| MD | 0.41 | 0.73 | 0.34 | 0.59 | 0.47 | 0.38 | 0.47 | full* | 0.27 | full* |
| CD | 0.33 | 0.53 | 0.36 | 0.39 | 0.29 | 0.43 | 0.57 | 0.37 | 0.41 | 0.66 |
| Tensile Strength (N/cm) | | | | | | | | | | |
| MD | 11.7 | 13.7 | 11.4 | 11.7 | 13.1 | 14.4 | 10.2 | 9.8 | 10.5 | 11.7 |
| CD | 2.5 | 2.3 | 2.3 | 2.5 | 1.8 | 2.1 | 1.8 | 2.1 | 1.8 | 1.9 |
| Elongation (%) | | | | | | | | | | |
| MD | 61 | 66 | 88 | 80 | 67 | 60 | 60 | 80 | 65 | 66 |
| CD | 103 | 106 | 104 | 81 | 106 | 67 | 108 | 96 | 107 | 109 |
| Pinhole Seepage | None | None | None | None | None | None | None | None | None | None |
| Gurley Hill Air Porosity (sec) | >3600 | >3600 | — | — | >3600 | >3600 | — | — | >3600 | >3600 |

*full bond had peel strength > 0.75 N/cm

Examples 18–31

Examples 18–31 were conducted to determine the effect of various process conditions on composite sheet properties. Examples 18–30 do not attempt to optimize end product properties. A film composition was prepared by dry blending 50% Hytrel® 8206, 33% by weight Hytrel® 8171, 4% by weight of another copolyether ester thermoplastic elastomer (Hytrel® 4056 sold by DuPont; melting temperature 150° C., vicat softening temperature 108° C., and a shore hardness of 40D) containing 50% by weight Ti-Pure® R960 titanium dioxide, and 13% by weight Bynel® 50E561. Ti-Pure® is a registered trademark of DuPont. The composition was fed to a melt extrusion coating line including a single screw extruder running at 20 rpm with a helical screw configuration. The zones of the extruder were heated to the temperature set forth in Table 2. The molten polymer mixture was fed to a film die with a width of about 35 cm that was maintained at same temperature as the extruder. The blend was extruded under the conditions set forth in Table 2, below, onto a moving fibrous sheet. The film composition joined the fiber sheet at a nip, as shown in FIG. 3, that was spaced about 9 cm (3.5 in) from the opening of the die.

The fibrous sheet was either a carded nonwoven ("C") or a spunbonded nonwoven ("S"). The carded sheet was made of carded polypropylene staple fiber, with fiber lengths generally ranging between 2.5 cm and 7.5 cm, that had been airlayed and thermal bonded. The polypropylene fiber sheet had a basis weight of 0.0305 kg/m$^2$ (0.9 oz/yd$^2$), a tensile strength of 8.3 N/cm (4.73 lb/in) in the machine direction and 1.5 N/cm (0.86 lb/in) in the cross direction, and an elongation of 73% in the machine direction and 95% in the cross direction. The spunbonded sheet was a spunbonded polypropylene with a basis weight of 0.0288 kg/m$^2$ (0.85 oz/yd$^2$), a tensile strength of 11.4 N/cm (6.5 lb/in) in the machine direction and 2.5 N/cm (1.4 lb/in) in the cross direction, and an elongation of 92% in the machine direction and 93% in the cross direction. In the Examples in Tables 2 and 3 for which "corona treatment" is indicated, before the fibrous sheet and the moisture vapor permeable film are joined, the fibrous sheet was passed at a sheet speed of 15 m/min through a Model RX-8 Corona Surface Treater manufactured by ENI Power Systems, Inc., that was set at a frequency of 25 kHz, and a power of 500–600 Watts.

Processing paramaters were controlled to determine how changing individual processing conditions impacted the sheet properties of peel strength, moisture vapor transmission, and dynamic barrier.

Examples 18–21 together demonstrate how increasing the temperature of the rolls 34 and 36 improve the peel strength of the composite sheet.

Examples 18, 22 and 23 together demonstrate how increasing the temperature of the die 38 through which the film composition is extruded improve the peel strength of the composite sheet.

Examples 24–26 together show how increasing the film thickness by slowing the line speed improves the peel strength of the composite sheet.

Examples 25 and 27 together demonstrate how the use of a more fibrous carded sheet material improves the peel strength of the composite sheet.

Examples 28, 29 and 30 show how increasing the temperature of the nip rolls 34 and 36 (FIG. 3) improves peel strength of the sheet, but also reduces moisture vapor transmission through the composite sheet. Differential Scanning Calorimetry measurements of the heat of fusion suggest that at the lower roll temperatures of Example 28, the film morphology is more amorphous, as compared to a more crystalline film morphology generated at the higher roll temperatures of Example 30. Thus, it appears that a more amorphous film morphology generated with lower roll temperatures results in a higher moisture vapor transmission rate.

Examples 25 and 31 show how increasing the pressure applied against the nip rolls 34 and 36 improves the peel strength of the sheet. In Example 31, a 138 kPa (20 psi) pressure was used in the pneumatic system to press roll 34 against roll 36. In Example 25, all processing conditions were the same as in Example 31 except that the pressure was 550 kPa (80 psi), as was also applied in Examples 18–30, such that the nip force in Example 25 was significantly greater than the nip force in Example 31. The increased nip force resulted in an increase in peel strength.

The fibrous sheet was a carded nonwoven ("C") made of carded polypropylene staple fiber, with fiber lengths generally ranging between 2.5 cm and 7.5 cm, that had been airlayed and thermal bonded. The polypropylene fiber sheet had a basis weight of 0.0305 kg/m² (0.9 oz/yd²), a tensile strength of 8.3 N/cm (4.73 lb/in) in the machine direction and 1.5 N/cm (0.86 lb/in) in the cross direction, and an elongation of 73% in the machine direction and 95% in the cross direction. Processing conditions were optimized such that peel strengths of from 0.08 to 0.29 N/cm were obtained without the addition of a polyolefin or a compatibilizer to the polyether ester polymer of the moisture permeable film layer material.

TABLE 2

| | Example | | | | | | |
|---|---|---|---|---|---|---|---|
| | 18 | 19 | 20 | 21 | 22 | 23 | 24 |
| Roll Temperature at Nip (° C.) | 40 | 15 | 76 | 115 | 42 | 42 | 40 |
| Extruder and Die Temperature (° C.) | 220 | 220 | 220 | 220 | 240 | 260 | 220 |
| Line Speed (m/min) | 13 | 13 | 13 | 13 | 13 | 13 | 18 |
| Substrate Composition | C | C | C | C | C | C | C |
| Corona Treated | Yes | Yes | Yes | Yes | Yes | Yes | No |
| Film Thickness (micron) | 22 | 22 | 22 | ~22 | 26 | ~22 | 16 |
| Peel Strength (N/cm) | 0.06 | 0.04 | 0.25 | Full | 0.27 | Full | 0.01 |
| MVTR(g/m²/24 hr) | 2700 | 2600 | 2400 | 2600 | 2400 | 2300 | 3100 |
| Dynamic Impact (g/m² @ 2400 J/m²) | 0.0 | 0.0 | 0.0 | 87* | 0.01 | 1.34* | 0.07 |

| | Example | | | | | | |
|---|---|---|---|---|---|---|---|
| | 25 | 26 | 27 | 28 | 29 | 30 | 31 |
| Roll Temperature at Nip (° C.) | 40 | 40 | 40 | 10 | 40 | 60 | 40 (138 kPa pressure) |
| Extruder and Die Temperature (° C.) | 220 | 220 | 220 | 220 | 220 | 220 | 220 |
| Line Speed (m/min) | 13 | 10 | 13 | 13 | 13 | 13 | 13 |
| Substrate Composition | C | C | S | C | C | C | C |
| Corona Treated | No | No | No | Yes | Yes | Yes | No |
| Film Thickness (micron) | 23 | 29 | 21 | 22 | 30 | 28 | 22 |
| Peel Strength (N/cm) | 0.07 | 0.23 | 0.03 | 0# | 0.23 | 0.61 | 0.04 |
| MVTR (g/m²/24 hr) | 2600 | 2400 | 2800 | 2800 | 2700 | 2500 | 2800 |
| Dynamic Impact (g/m² @ 2400 J/m²) no hold/10 sec hold | 0.0 | 0.13 | 0.1 | 0.03 | — | 0.28 | 0.08 |

*pinholes present due to excessive bonding
Had sticking to small roll, may have reduced peel.

Examples 32–34

A film composition was prepared by dry blending 57.5% by weight of a copolyether ester thermoplastic elastomer (Hytrel® 8206), 38% by weight of another copolyether ester thermoplastic elastomer (Hytrel® 8171), and 4.5% by weight of another copolyether ester thermoplastic elastomer (Hytrel® 4056) containing 50% by weight Ti-Pure® R960 titanium dioxide pigment. The composition was fed to a melt extrusion coating line including a single screw extruder running at 20 rpm with a helical screw configuration . The heating zones of the extruder were set to 220° C. The molten polymer mixture was fed to a film die with a width of about 35 cm that was maintained at 220°. The blend was extruded under the conditions set forth in Table 3, below, onto a moving fibrous sheet. The film composition joined the fiber sheet at a nip, as shown in FIG. 3, that was spaced about 9 cm (3.5 in) from the opening of the die.

TABLE 3

| | Example | | |
|---|---|---|---|
| | 32 | 33 | 34 |
| Roll Temperature at Nip (° C.) | 40 | 40 | 40 |
| Extruder and Die Temperature (° C.) | 220 | 220 | 220 |
| Line Speed (m/min) | 13 | 13 | 13 |

TABLE 3-continued

| | Example | | |
|---|---|---|---|
| | 32 | 33 | 34 |
| Substrate Composition | C | C | C |
| Corona Treated | Yes | Yes | No |
| Film Thickness (micron) | 31 | 24 | 25 |
| Peel Strength (N/cm) | 0.29 | 0.08 | 0.10 |
| MVTR (g/m$^2$/24 hr) | 3600 | 3600 | 3500 |
| Dynamic Impact (g/m$^2$ @ 2400 J/m$^2$) | 0.0 | 0.0 | 0.0 |

Example 35

A film composition was prepared as in Examples 19–31. The composition was fed to a melt extrusion coating line including a single screw extruder running at 20 rpm with a helical screw configuration. The heating zones of the extruder were set to 220° C. The molten polymer mixture was fed to a film die with a width of about 35 cm that was maintained at 220°. The blend was extruded under the conditions set forth below, between two moving fibrous sheets. The film composition joined the fiber sheets at a nip, similar to that shown in FIG. 3. However, one fibrous sheet was fed into the nip on each of the rolls 34 and 36, and both fibrous sheets joined the film layer at the nip. The opening of the nip was spaced about 9 cm (3.5 in) from the opening of the die.

Each of the fibrous sheets was a carded nonwoven ("C") made of carded polypropylene staple fiber, with fiber lengths generally ranging between 2.5 cm and 7.5 cm, that had been airlayed and thermal bonded. The polypropylene fiber sheet had a basis weight of 0.0305 kg/m$^2$ (0.9 oz/yd$^2$), a tensile strength of 8.3 N/cm (4.73 lb/in) in the machine direction and 1.5 N/cm (0.86 lb/in) in the cross direction, and an elongation of 73% in the machine direction and 95% in the cross direction. The composite sheet formed was like that shown in FIG. 2. Processing conditions and product properties are listed on Table 4 below.

TABLE 4

| Example | 35 |
|---|---|
| Roll Temperature at Nip (° C.) | 70 |
| Extruder and Die Temperature (° C.) | 220 |
| Line Speed (m/min) | 13 |
| Substrate Composition | C (both sheets) |
| Corona Treated | Yes |
| Film Thickness (micron) | 24 |
| Peel Strength (N/cm) | 0.11 (side A) / 0.16 (side B) |
| MVTR (g/m$^2$/24 hr) | 2300 |
| Dynamic Impact (g/m$^2$ @ 2400 J/m$^2$) | 0.10 |

Examples 36–39

A first polymer composition was prepared as in Examples 19–31. This first polymer composition was fed to a 38 mm diameter extruder at a temperature of 220° C. which was run at 20 rpm. The output of this 38 mm extruder was connected to a melt combining block. A second polymer composition comprised of 100% Hytrel® 4778 (melting point 208° C., vicat softening temperature 175° C., and Shore hardness of 47D) was fed to a 25 mm diameter extruder that was also connected to the same melt combining block. This 25 mm diameter extruder was also operated at a temperature of 220° C. In Examples 36–39, the speed of the 25 mm extruder was varied from 20 rpm to 1.5 rpm to generate films wherein the thickness of the layer of the second polymer composition varied. The coextruded layers were combined in the melt combining block. The layers were then passed through a die that was connected to the combining block. The die had a 35 cm wide die block that was heated to about 220° C.

A bonded bicomponent film was formed and exited the die. The layer of the first polymer composition maintained a nominal thickness of about 22 microns in each of the Examples 36–39. The thickness of the layers of the second polymer composition was between 4 and 0.2 microns. This film was bonded with a hot melt adhesive in a spiral spray pattern to a polyethylene 30.5 micron (1.2 mil) film (from Tredegar Film Products) of the type used in backsheets of absorbent articles. The hot melt adhesive was a linear SIS adhesive (Findley H2031) of the type that is currently being used in diaper manufacturing.

To measure the "construction peel strength" of the resulting bond between the polyethylene film and the second polymer composition, 1 inch wide strips of the two materials were prepared and facially bonded to one another over an area measuring one square inch, leaving an opposed pair of unbonded flaps on at least one end of the strips long enough to span the gage length of the testing unit. The adhesive utilized was a linear SIS adhesive commercially available from Findley Adhesives under the designation H2031, applied at a 0.009 grams/square inch add-on level in a spiral spray pattern. Three samples were prepared for each test sequence, with the reported results comprising an average of the results for the three samples. An Instron table model tester was utilized with a 5 pound load cell, a 2 inch gage length, and a crosshead speed of 20 inches per minute, in a manner generally consistent with the Elongation to Break test described above. Opposing unbonded flaps of the two materials were clamped in the respective clamps of the tester, with the second polymer composition in the upper clamp. Specimens were evaluated at the point of failure when delamination of the adhesive bond or the substrates themselves occurred.

Bicomponent film/polyethylene constructions were prepared according to the following conditions to obtain the following properties:

TABLE 5

| | Example | | | |
|---|---|---|---|---|
| | 36 | 37 | 38 | 39 |
| Extruder Speed (rpm) (25 mm extruder) | 20 | 10 | 5 | 1.5 |
| Thickness-second film layer (microns) | 4 | 1.7 | 0.7 | 0.2 |
| MVTR-bicomponent film (g/m$^2$/day) | 2700 | 2800 | 2900 | 2900 |
| Construction peel strength - Dry (N/cm) | 2.47 | 1.71 | 1.70 | 1.43 |
| Construction peel strength - Wet* (N/cm) | 1.78 | 1.93 | 1.73 | 1.63 |

*Wet state means test sample was soaked in distilled water for 30 minutes.

Comparative Example 1

A sample of Exxon Exxair XFB-100W microporous film, available from Exxon Chemical Company of Buffalo Grove, Ill., USA, was tested for moisture vapor transmission rate, dynamic fluid transmission, microbial barrier for sterile packaging, and liquid moisture seepage. The properties measured were as follows:

| | |
|---|---|
| MVTR (g/m$^2$/24 hr) | 4000 |
| Dynamic Impact (g/m$^2$ @ 2400 J/m$^2$) | 0.97 |
| Microbial Barrier | *Bacillus subtilis* bacteria passage recorded in six of six samples tested after 15 minute exposure. (38.6 cm Hg vacuum; 2.8 l/min flow rate) |
| Moisture Seepage | Dye apparent on blotter indicating passage of liquid. |

It will be apparent to those skilled in the art that modifications and variations can be made in breathable composite sheet material of this invention. The intention in its broader aspects is, therefore, not limited to the specific details or the illustrative examples described above. Thus, it is intended that all matter contained in the foregoing description drawings and examples shall be interpreted as illustrative and not in a limiting sense.

What is claimed is:

1. A breathable composite sheet material comprising a substrate and a thermoplastic film adhered directly to the substrate,
    said thermoplastic film comprising
        at least 50% by weight of a Fraction A consisting essentially of polymer from the group of block copolyether esters, block copolyether amides and polyurethanes,
        at least 5% by weight of a Fraction B consisting essentially of polymer that is incompatible with Fraction A, and
        at least 0.1% by weight of a Fraction C consisting essentially of a compatibilizer for Fractions A and B; and
    said substrate comprising at least 50% by weight of a polymer that is incompatible with film Fraction A.

2. The composite sheet material of claim 1 wherein film Fraction B is comprised of at least 50% by weight of at least one of a homopolymer of an alpha-olefin, a copolymer or terpolymer containing an alpha-olefin and one or more other monomers, and a block copolymer of a vinylarene and a conjugated diene.

3. The composite sheet material of claim 2 wherein film Fraction C consists essentially of homopolymers, copolymers and terpolymers with backbones that are compatible with Fraction B, said backbones being grafted with a monomer having a functional group that is compatible with Fraction A.

4. The composite sheet material of claim 3 wherein film Fraction C is a polymer with a backbone identical to Fraction B, said backbone being grafted with monomer selected from the group of alpha- and beta-ethylenically unsaturated carbonic acids and anhydrides, and derivatives thereof.

5. The composite sheet material of claim 1 wherein the substrate is a fibrous nonwoven sheet comprised of at least 50% by weight of a polyolefin polymer.

6. The composite sheet material of claim 5 wherein the substrate is a nonwoven sheet made from a fibrous web comprised of at least 50% by weight polypropylene.

7. The composite sheet material of claim 5 wherein the substrate is a nonwoven sheet made from a fibrous web comprised of at least 50% by weight polyethylene.

8. The composite sheet material of claim 1 wherein film Fraction is a block copolyether ester, film Fraction B is polypropylene, film Fraction C is a grafted polymer having a backbone of polypropylene that is grafted with maleic anhydride, and the substrate is a nonwoven spunbonded sheet made from a fibrous web comprised of at least 50% by weight polypropylene.

9. The composite sheet material of claim 8 wherein the thermoplastic film comprises, by weight, 50% to 95% film Fraction A, 5% to 50% film Fraction B, and 0.1% to 15% film Fraction C.

10. The composite sheet material of claim 9 wherein the thickness of the thermoplastic film is in the range of 5 to 50 microns, and the sheet material has a moisture vapor transmission rate of at least 200 g/m$^2$/24 hrs (by method ASTM E96-B), and a peel strength per unit thickness of the thermoplastic film of the sheet material is at least 0.003 N/cm-micron.

* * * * *

UNITED STATES PATENT AND TRADEMARK OFFICE
CERTIFICATE OF CORRECTION

PATENT NO.    : 6,677,258 B2
DATED         : January 13, 2004
INVENTOR(S)   : Carroll Nora L. et al.

Page 1 of 1

It is certified that error appears in the above-identified patent and that said Letters Patent is hereby corrected as shown below:

Title page,
Insert Item     Related U.S. Application Data
        -- [60]  This appliation is a Continuation-in-Part of U.S. Serial No. 08/655,046, filed May 29, 1996 (now abandoned); and a Continuation-in-Part of U.S. Serial No. 08/744,487, filed November 6, 1996 (now abandoned); and entered the U.S. National Phase under 35 U.S.C. 371 based upon PCT/US97/09215, filed in the U.S. Receiving Office on May 29, 1997. --
Item [65], Prior Publication Data, add -- WO 97/45259 4 December 1997 --

Column 39,
Line 27, after "substrate" insert -- in the absence of an adhesive --.
Line 40, delete "polymer" and insert -- polyolefin --.

Column 40,
Line 26, after "Fraction" (first occurrence) insert -- A --.

Signed and Sealed this

Fourteenth Day of September, 2004

JON W. DUDAS
*Director of the United States Patent and Trademark Office*